US010894255B2

(12) United States Patent
Hou et al.

(10) Patent No.: US 10,894,255 B2
(45) Date of Patent: Jan. 19, 2021

(54) LEUKOCYTE AND MICROPARTICLES FRACTIONATION USING MICROFLUIDICS

(71) Applicant: Nanyang Technological University, Singapore (SG)

(72) Inventors: Han Wei Hou, Singapore (SG); Bernhard Otto Boehm, Singapore (SG); Hui Min Tay, Singapore (SG); Say Chye Joachim Loo, Singapore (SG)

(73) Assignee: Nanyang Technological University, Singapore (SG)

( * ) Notice: Subject to any disclaimer, the term of this patent is extended or adjusted under 35 U.S.C. 154(b) by 464 days.

(21) Appl. No.: 15/741,149

(22) PCT Filed: Jun. 30, 2016

(86) PCT No.: PCT/SG2016/050306
§ 371 (c)(1),
(2) Date: Dec. 29, 2017

(87) PCT Pub. No.: WO2017/003380
PCT Pub. Date: Jan. 5, 2017

(65) Prior Publication Data
US 2018/0185846 A1    Jul. 5, 2018

(30) Foreign Application Priority Data

Jul. 2, 2015    (SG) ............................ 10201505259T
Dec. 18, 2015    (SG) ............................ 10201510460P

(51) Int. Cl.
*B01L 3/00*    (2006.01)
*G01N 33/50*    (2006.01)
(Continued)

(52) U.S. Cl.
CPC ... *B01L 3/502776* (2013.01); *B01L 3/502761* (2013.01); *G01N 33/5029* (2013.01);
(Continued)

(58) Field of Classification Search
None
See application file for complete search history.

(56) References Cited

U.S. PATENT DOCUMENTS 8,208,138 B2 * 6/2012 Papautsky et al. .... G01N 15/02
356/335
10,077,462 B2 * 9/2018 Hou et al. ................ C12Q 1/24
2011/0096327 A1 4/2011 Papautsky et al.

FOREIGN PATENT DOCUMENTS

WO    2013/181615 A1    12/2013
WO    2014/152643 A2    9/2014

OTHER PUBLICATIONS

Nivedita et al. "Continuous separation of blood cells in spiral microfluidic devices", Biomicrofluidics 7, 054101 (2013), of record in IDS, and Hou et al. "Isolation and retrieval of circulating tumor cells using centrifugal forces", Scientific Reports, 3, 1259 (2013). (Year: 2013).*

(Continued)

Primary Examiner — Kevin K Hill
Assistant Examiner — James Joseph Graber
(74) Attorney, Agent, or Firm — Seed IP Law Group LLP

(57) ABSTRACT

This invention relates to a method for separating blood cells comprising the steps of: (a) lysing red blood cells of a blood sample and diluting said sample; (b) providing a microfluidic device comprising a spiral-shaped flow channel having at least a first end and a second end, wherein said flow channel has two inlet ports at or near said first end and at least two outlet ports at or near said second end, wherein one of the two inlet ports is located at the inner wall of the spiral-shaped flow channel and the other inlet port is located (Continued)

at the outer wall of the spiral-shaped flow channel and at least one of the outlet ports is connected to a container allowing the storage of blood cells; (c) introducing the sample of step (a) into the inlet port located at the outer wall of the spiral-shaped flow channel and introducing a sheath fluid into the inlet port located at the inner wall of the spiral-shaped flow channel; (d) driving said sample and the sheath fluid through the spiral-shaped flow channel; and (e) recovering the blood cell in the at least one container connected to the at least one outlet port. The present invention also relates to coupling above described method of purifying neutrophils in the native state with a method for diagnosing diabetes or an inflammatory disease in a subject, which involves further investigation of neutrophils by determining their rolling speed, the neutrophil circularity (NC) index and/or the expression of markers, such as intracellular reactive oxygen species (ROS), CD1 1 b or PSGL-1.

12 Claims, 20 Drawing Sheets

(51) Int. Cl.
G01N 33/569 (2006.01)
G01N 33/49 (2006.01)

(52) U.S. Cl.
CPC ..... *G01N 33/5091* (2013.01); *G01N 33/5094* (2013.01); *G01N 33/56972* (2013.01); *B01L 2200/0636* (2013.01); *B01L 2200/0652* (2013.01); *B01L 2300/0864* (2013.01); *B01L 2300/0877* (2013.01); *G01N 33/491* (2013.01); *G01N 2800/042* (2013.01); *G01N 2800/7095* (2013.01)

(56) References Cited

OTHER PUBLICATIONS

Lin-Yue et al., "Neutrophil adhesion on phosphorylcholine-containing polyurethanes", Biomaterials, 19 (1998) 31-40. (Year: 1998).*
Sackmann et al. "Characterizing asthma from a drop of blood using neutrophil chemotaxis", Proc Natl Acad Sci U S A. Apr. 22, 2014; 111(16): 5813-5818. (Year: 2014).*
Delamaire et al., "Impaired Leucocyte Functions in Diabetic Patients", Diabetic Medicine, 1997; 14: 29-34. (Year: 1997).*
Wierusz-Wysocka, et al., "Evidence of Polymorphonuclear Neutrophils (PMN) Activation in Patients With Insulin-Dependent Diabetes Mellitus", Journal of Leukocyte Biology, 42:519-523 (1987). (Year: 1987).*
Lawrence et al. "Neutrophils Roll on E-Selectin", Journal of Immunology, vol. 151, 6338-6346, No. 11, 1993. (Year: 1993).*
Hou et al. "Isolation and retrieval of circulating tumor cells using centrifugal forces", Scientific Reports, 3, 1259 (2013). (Year: 2013).*
Supplementary Information of Hou et al. "Isolation and retrieval of circulating tumor cells using centrifugal forces", Scientific Reports, 3, 1259 (2013). (Year: 2013).*
Johnston et al., "Dean flow focusing and separation of small microspheres within a narrow size range", Microfluid Nanofluid, (Jan. 2014) 17:509-518. (Year: 2014).*
Sun et al., "Size-based hydrodynamic rare tumor cell separation in curved microfluidic channels", Biomicrofluidics, 7, 011802 (2013). (Year: 2013).*
Yamada et al., "Hydrodynamic filtration for on-chip particle concentration and classification utilizing microfluidics", Lab Chip, 2005, 5, 1233-1239. (Year: 2005).*

Alba-Loureiro et al., "Neutrophil function and metabolism in individuals with diabetes mellitus," Braz J Med Biol Res 40(8):1037-1044, 2007.
Alipour et al., "Leukocyte Activation by Triglyceride-Rich Lipoproteins," Arterioscler Thromb Vasc Biol 28(4):792-797, 2008.
Bagdade et al., "Impaired Leukocyte Function in Patients with Poorly Controlled Diabetes," Diabetes 23(1):9-15, 1974.
Bhagat et al., "Continuous particle separation in spiral microchannels using dean flows and differential migration," Lab Chop 8:1906-1914, 2008.
Bhagat et al., "Enhanced particle filtration in straight microchannels using shear-modulated inertial migration," Phys. Fluids 20:101702, 2008. (5 pages).
Bhagat et al., "Inertial microfluidics for continuous particle filtration and extraction," Microfluid Nanofluid 7:217-226, 2009.
Bhagat et al., "Microfluidics for cell separation," Med Biol Eng Comput 48:999-1014, 2010.
Bose et al., "Affinity flow fractionation of cells via transient interactions with asymmetric molecular patterns," Scientific Reports 3:2329, 2013. (8 pages).
Cavalot et al., "White Blood Cell Count Is Positively Correlated With Albumin Excretion Rate in Subjects With Type 2 Diabetes," Diabetes Care 25(12):2354-2355, 2002.
Chang et al., "Biomimetic technique for adhesion-based collection and separation of cells in a microfluidic channel," Lab Chip 5:64-73, 2005.
Crutchfield et al., "CD11b/CD18-coated microspheres attach to E-selectin under flow," Journal of Leukocyte Biology 67:196-205, 2000.
Davenpeck et al., "Activation of Human Leukocytes Reduces Surface P-Selectin Glycoprotein Ligand-1 (PSGL-1, CD162) and Adhesion to P-Selectin In Vitro," J Immunol 165:2764-2772, 2000.
Davis et al., "Deterministic hydrodynamics: Taking blood apart," PNAS 103(40):14779-14784, 2006.
Dean, "The Stream-line Motion of Fluid in a Curved Pipe," Phil. Mag. S. 7. 5(30):673-695, 1928.
Deans et al., ""Anti-Inflammatory" Drugs and Their Effects on Type 2 Diabetes," Diabetes Technology & Therapeutics 8(1):18-27, 2006.
Delamaire et al., "Impaired Leucocyte Functions in Diabetic Patients," Diabetic Medicine 14:29-34, 1997.
Di Carlo et al., "Continuous inertial focusing, ordering, and separation of particles in microchannels," PNAS 104(48):18892-18897, 2007.
Di Carlo et al., "Equilibrium Separation and Filtration of Particles Using Differential Inertial Focusing," Anal. Chem. 80(6):2204-2211, 2008.
Dorward et al., "Autofluorescence-based sorting: rapid and nonperturbing isolation of ultrapure neutrophils to determine cytokine production," Journal of Leukocyte Biology 94:193-202, 2013.
Dunzendorfer et al., "Mevalonate-Dependent Inhibition of Transendothelial Migration and Chemotaxis of Human Peripheral Blood Neutrophils by Pravastatin," Circulation Research 81(6):963-969, 1997. (19 pages).
Elkord et al., "Human monocyte isolation methods influence cytokine production from in vitro generated dendritic cells," Immunology 114:204-212, 2005.
Ernst et al., "Altered Red and White Blood Cell Rheology in Type II Diabetes," Diabetes 35:1412-1415, 1986.
Friedman et al., "The Leukocyte Count as a Predictor of Myocardial Infarction," The New England Journal of Medicine 290(23):1275-1278, 1974.
Fukuda et al., "Centrifugation attenuates the fluid shear response of circulating leukocytes," Journal of Leukocyte Biology 72:133-139, 2002.
Green et al., "Shear-Dependent Capping of L-Selectin and P-Selectin Glycoprotein Ligand 1 by E-Selectin Signals Activation of High-Avidity $\beta_2$ -Integrin on Neutrophils," J Immunol 172:7780-7790, 2004.
Hartaigh et al., "Which leukocyte subsets predict cardiovascular mortality? From the LUdwigshafen RIsk and Cardiovascular Health (LURIC) Study," Atherosclerosis 224:161-169, 2012.
Heikali et al., "A Niche for Microfluidics in Portable Hematology Analyzers," JALA 15(4):319-328, 2010.

(56) References Cited

OTHER PUBLICATIONS

Hirsch et al., "Metformin Selectively Targets Cancer Stem Cells, and Acts Together with Chemotherapy to Block Tumor Growth and Prolong Remission," *Cancer Res* 69(19):7507-7511, 2009.
Hou et al., "Isolation and retrieval of circulating tumor cells using centrifugal forces," *Scientific Reports* 3:1259, 2013. (8 pages).
International Search Report and Written Opinion, dated Sep. 9, 2016, for International Application No. PCT/SG2016/050306, 14 pages.
Jung et al., "Transit Time of Leukocytes Rolling through Venules Controls Cytokine-induced Inflammatory Cell Recruitment In Vivo," *J. Clin. Invest.* 102(8):1526-1533, 1998.
Kolaczkowska et al., "Neutrophil recruitment and function in health and inflammation," *Nature Reviews Immunology* 13:159-175, 2013.
Kotz et al., "Clinical microfluidics for neutrophil genomics and proteomics," *Nature Medicine* 16(9):1042-1047, 2010. (8 pages).
Kowalczyk et al., "Nanoseparations: Strategies for size and/or shape-selective purification of nanoparticles," *Current Opinion in Colloid & Interface Science* 16:135-148, 2011.
Kuntaegowdanahalli et al., "Inertial microfluidics for continuous particle separation in spiral microchannels," *Lab Chip* 9:2973-2980, 2009.
Lavoie-Lamoureux et al., "IL-4 activates equine neutrophils and induces a mixed inflammatory cytokine expression profile with enhanced neutrophil chemotactic mediator release ex vivo," *Am J Physiol Lung Cell Mol Physiol* 299: L472-L482, 2010.
Lawrence et al., "Neutrophils Roll on E-Selectin," *J Immunol* 151(11):6338-6346, 1993.
Ley et al., "Getting to the site of inflammation: the leukocyte adhesion cascade updated," *Nature Reviews Immunology* 7:678-689, 2007.
Mowat et al., "Chemotaxis of Polymorphonuclear Leukocytes from Patients with Diabetes Mellitus," *The New England Journal of Medicine* 284(12):621-627, 1971.
Murai et al., "Low Cholesterol Triggers Membrane Microdomain-dependent CD44 Shedding and Suppresses Tumor Cell Migration," *Journal of Biological Chemistry* 286(3):1999-2007, 2011.
Nguyen et al., *Fundamentals and Applications of Microfluidics*, Artech House, 2006, Chapter 3, "Fabrication Techniques for Microfluidics," pp. 55-115.
Nguyen et al., *Fundamentals and Applications of Microfluidics*, Artech House, 2006, Chapter 7, "Microfluidics for Internal Flow Control: Micropumps," pp. 255-309.
Nguyen et al., *Fundamentals and Applications of Microfluidics*, Artech House, 2006, Chapter 11, "Microfluidics for Life Sciences and Chemistry: Microdispensers," pp. 395-417.
Ookawara et al., "Numerical study on development of particle concentration profiles in a curved microchannel," *Chemical Engineering Science* 61:3714-3724, 2006.
Park et al., "Activation of AMPK Enhances Neutrophil Chemotaxis and Bacterial Killing," *Mol Med* 19:387-398, 2013.
Pécsvarády et al., "Decreased Polymorphonuclear Leukocyte Deformability in NIDDM," *Diabetes Care* 17(1):57-63, 1994.
Petersson et al., "Free Flow Acoustophoresis: Microfluidic-Based Mode of Particle and Cell Separation," *Anal. Chem.* 79:5117-5123, 2007.
Pickup, "Inflammation and Activated Innate Immunity in the Pathogenesis of Type 2 Diabetes," *Diabetes Care* 27(3):813-823, 2004.
Pommer et al., "Dielectrophoretic separation of platelets from diluted whole blood in microfluidic channels," *Electrophoresis* 29:1213-1218, 2008.
Pradhan et al., "C-Reactive Protein, Interleukin 6, and Risk of Developing Type 2 Diabetes Mellitus," *JAMA* 286(3):327-334, 2001.
Rijcken et al., "Immunoblockade of PSGL-1 attenuates established experimental murine colitis by reduction of leukocyte rolling," *Am J Physiol Gastrointest Liver Physiol* 287:G115-G124, 2004.
Schaff et al., "Vascular mimetics based on microfluidics for imaging the leukocyte-endothelial inflammatory response," *Lab Chip* 7:448-456, 2007.

Shah et al., "Quantifying the Risk of Infectious Diseases for People With Diabetes," *Diabetes Care* 26(2):510-513, 2003.
Silbernagel et al., "Additional Use of Glycated Hemoglobin for Diagnosis of Type 2 Diabetes in People Undergoing Coronary Angiography Reveals a Subgroup at Increased Cardiovascular Risk," *Diabetes Care* 34:2471-2473, 2011.
Simon et al., "Neutrophil Tethering on E-Selectin Activates $\beta_2$ Integrin Binding to ICAM-1 Through a Mitogen-Activated Protein Kinase Signal Transduction Pathway," *J Immunol* 164:4348-4358, 2000.
Sollier et al., "Rapid prototyping polymers for microfluidic devices and high pressure injections," *Lab Chip* 11:3752-3765, 2011.
Stehouwer et al., "Increased Urinary Albumin Excretion, Endothelial Dysfunction, and Chronic Low-Grade Inflammation in Type 2 Diabetes," *Diabetes* 51:1157-1165, 2002.
Tong et al., "White Blood Cell Count Is Associated With Macro- and Microvascular Complications in Chinese Patients With Type 2 Diabetes," *Diabetes Care* 27(1):216-222, 2004.
Wierusz-Wysocka et al., "Evidence of Polymorphonuclear Neutrophils (PMN) Activation in Patients With Insulin-Dependent Diabetes Mellitus," *Journal of Leukocyte Biology* 42:519-523, 1987.
Wild et al., "Global Prevalence of Diabetes: Estimates for the year 2000 and projections for 2030," *Diabetes Care* 27(5):1047-1053, 2004.
Wu et al., "Separation of Leukocytes from Blood Using Spiral Channel with Trapezoid Cross-Section," *Anal. Chem.* 84:9324-9331, 2012.
Xia et al., "P-selectin glycoprotein ligand-1-deficient mice have impaired leukocyte tethering to E-selectin under flow," *Journal of Clinical Investigation* 109(7):939-950, 2002.
Yager et al., "Microfluidic diagnostic technologies for global public health," *Nature* 442:412-418, 2006.
Yago et al., "E-selectin engages PSGL-1 and CD44 through a common signaling pathway to induce integrin $\alpha_L\beta_2$ -mediated slow leukocyte rolling," *Blood* 116(3):485-494, 2010.
Yang et al., "Letter to the Editor: Centrifugation of Human Lung Epithelial Carcinoma A549 Cells Up-Regulates Interleukin-1$\beta$ Gene Expression," *Clinical and Diagnostic Laboratory Immunology* 9(5):1142-1143, 2002.
Zhu et al., "Eosinophil Inversely Associates with Type 2 Diabetes and Insulin Resistance in Chinese Adults," *PLoS One* 8(7):e67613, 2013 (6 pages).
English Translation of Office Action, dated Apr. 7, 2020, of Japanese Application No. 2017-567746, 6 pages.
Nivedita et al, "Continuous separation of blood cells in spiral microfluidic devices," *Biomicrofluidics* 7:054101, 2013. (14 pages).
Hou et al., "Direct detection and drug-resistance profiling of bacteremias using inertial microfluidics," *Lab Chip* 15:2297-2307, May 2015.
Johnston et al., "Dean flow focusing and separation of small microspheres within a narrow size range,"*Microfluid Nanofluid* 17:509-518, Jan. 2014.
Khoo et al., "Clinical Validation of an Ultra High-Throughput Spiral Microfluidics for the Detection and Enrichment of Viable Circulating Tumor Cells," *PLOS ONE* 9(7):e99409, Jul. 2014. (8 pages).
Menart-Houtermans et al., "Leukocyte Profiles Differ Between Type 1 and Type 2 Diabetes and Are Associated With Metabolic Phenotypes: Results From the German Diabetes Study (GDS)," *Diabetes Care* 37:2326-2333, Aug. 2014.
Sackmann et al., "Characterizing asthma from a drop of blood using neutrophil chemotaxis,"*PNAS* 111(16):5813-5818, Apr. 2014.
Sackmann et al., "The present and future role of microfluidics in biomedical research," *Nature* 507:181-189, Mar. 2014.
Thévenot et al., "Analysis of the Human Adult Urinary Metabolome Variations with Age, Body Mass Index, and Gender by Implementing a Comprehensive Workflow for Univariate and OPLS Statistical Analyses," *J. Proteome Res.* 14(8):3322-3335, Jun. 2015. (15 pages).
Warkiani et al., "An ultra-high-throughput spiral microfluidic biochip for the enrichment of circulating tumor cells," *Analyst* 139:3245-3255, Apr. 2014.

(56) References Cited

OTHER PUBLICATIONS

Yeo et al., "Interference-free Micro/nanoparticle Cell Engineering by Use of High-Throughput Microfluidic Separation," *ACS Appl. Mater. Interfaces* 7:20855-20864, Sep. 2015. (11 pages).

* cited by examiner

Figure 7

Characteristics of healthy and T2DM patients

| Characteristics | T2DM (n = 16) | Healthy (n = 13) | $P*$ |
|---|---|---|---|
| Age (Range) | 56 (34 - 64) | 31 (22 - 37) | - |
| CRP, mg/L | 3.544 (1.123) | 1.455 (0.844) | 0.047 |
| HbA1c, % | 9.544 (0.426) | n.a. | - |
| Fasting Glucose (mmol/L) | 10.914 (1.130) | 5.033 (0.108) | 0.0001 |
| Total-C (mmol/L) | 4.244 (0.152) | 4.893 (0.279) | NS |
| HDL-C (mmol/L) | 1.094 (0.047) | 1.335 (0.095) | 0.019 |
| LDL-C (mmol/L) | 2.420 (0.139) | 3.204 (0.287) | 0.02 |
| Triglyceride (mmol/L) | 1.894 (0.420) | 0.793 (0.155) | 0.0004 |

Average value shown with s.e.m. in parentheses, unless otherwise indicated. NS, Non-significant.

Figure 8

| Channel height (um) | Ratio of cell size to channel height ||
| --- | --- | --- |
| | Neutrophils/Monocytes (12um) | Lymphocytes (8um) |
| 90 | 0.133333333 | 0.088888889 |
| 100 | 0.12 | 0.08 |
| 110 | 0.109090909 | 0.072727273 |
| 115 | 0.104347826 | 0.069565217 |
| 120 | 0.1 | 0.066666667 |
| 130 | 0.092307692 | 0.061538462 |

Below 110 μm, inertial focusing in stronger for lymphocytes (ratio>0.07) and thus cannot be easily separated from neutrophils.

A)

B)

LEUKOCYTE AND MICROPARTICLES FRACTIONATION USING MICROFLUIDICS

FIELD OF THE INVENTION

The present invention lies in the field of biochemistry and relates to a method for separating blood cells comprising the steps of: (a) lysing red blood cells of a blood sample and diluting said sample; (b) providing a microfluidic device comprising a spiral-shaped flow channel having at least a first end and a second end, wherein said flow channel has two inlet ports at or near said first end and at least two outlet ports at or near said second end, wherein one of the two inlet ports is located at the inner wall of the spiral-shaped flow channel and the other inlet port is located at the outer wall of the spiral-shaped flow channel and at least one of the outlet ports is connected to a container allowing the storage of blood cells; (c) introducing the sample of step (a) into the inlet port located at the outer wall of the spiral-shaped flow channel and introducing a sheath fluid into the inlet port located at the inner wall of the spiral-shaped flow channel; (d) driving said sample and the sheath fluid through the spiral-shaped flow channel; and (e) recovering the blood cells in the at least one container connected to the at least one outlet port. The present invention also relates to a method for diagnosing diabetes or an inflammatory disease in a subject and to a microfluidic device.

BACKGROUND OF THE INVENTION

Small particle separation is an important sample preparation step in many applications ranging from material sciences (nanotechnology), environmental bio-sampling to bacterial diagnostics in clinical settings. Conventional separation strategies include centrifugation, sedimentation or membrane filtration which are limited by batch-mode processing and increasing difficulties when applied to separation of small micro/nanoparticles (<5 μm). Size-based separation of small particles is an attractive alternative since it is independent of particle properties (density, surface charges, and magnetic affinity) and can operate in a continuous flow manner. However, there is a lack of efficient and passive particle sorting methods which advocates the need to develop new separation technologies that can achieve small particle separation of closely spaced sizes.

Standard blood analysis in clinical settings relies on complete blood count (CBC) to assess inflammation status and limited strategies exist to characterize functional abnormalities in leukocytes (white blood cells) [Heikali, D. and D. Di Carlo, 2010. 15(4): p. 319-328]. A main reason behind is the lack of suitable isolation and assay methods to study cellular functions in a simple and reproducible manner. This is further aggravated by blood sample preparation difficulties using conventional leukocyte isolation methods (density gradient centrifugation and RBCs lysis) which require large blood volume (~10 mL) and may cause undesirable cell activation [Yang, J., et al., 2002. 9(5): p. 1142-1143]. In laboratory settings, immunophenotyping by flow cytometry is possible but is limited by cost, equipment access and laborious leukocyte purification procedures. It is thus critical to develop new tools for leukocyte studies to gain more information on the health status in addition to serum testing.

Diabetes mellitus (DM) is a prototypic dysmetabolic syndrome characterized by chronic hyperglycemia and remains a serious health burden globally with a predicted rise to 360 million by 2030 [Wild, S. et al. *Diabetes Care* 27, 1047-1053 (2004)]. In type 2 diabetes mellitus (T2DM), patients suffer from impaired glucose metabolism which results in low-grade inflammation and activation of the innate immune system, with an increased risk of cardiovascular complications [Stehouwer, C. D. A. et al. *Diabetes* 51, 1157-1165 (2002); Pradhan, A. D. et al. *JAMA* 286, 327-334 (2001); Pickup, J. C. *Diabetes Care* 27, 813-823 (2004); Silbernagel, G. et al. *Diabetes Care* 34, 2471-2473 (2011)]. While differential leukocyte count and C-reactive protein (CRP) level are routinely measured and are associated with cardiovascular mortality [Hartaigh, B. et al. *Atherosclerosis* 224, 161-169 (2012); Friedman, G. D. et al. *N. Engl. J. Med.* 290, 1275-1278 (1974)], macro/microvascular complications [Cavalot, F. et al. *Diabetes Care* 25, 2354-2355 (2002); Tong, P. C. et al. *Diabetes Care* 27, 216-222 (2004)] and metabolic phenotypes [Menart-Houtermans, B. et al. *Diabetes Care* 37, 2326-2333 (2014)] in diabetic patients, it is imperative to develop new cell-based biomarkers that can quantity specific immune functions in addition to leukocyte enumeration. Neutrophils, the key effector cells of the innate immune system, are known to play a pivotal role in T2DM pathogenesis as well as its associated vascular complications [Alba-Loureiro, T. C. et al. *Braz. J. Med. Biol. Res.* 40, 1037-1044 (2007)]. Various neutrophil dysfunctions have been reported in T2DM patients including cell stiffening [Ernst, E. & Matrai, A. *Diabetes* 35, 1412-1415 (1986); Pécsvarády, Z. et al. *Diabetes Care* 17, 57-63 (1994)], impaired chemotaxis [Mowat, A. G. & Baum, J. *N. Engl. J. Med.* 284, 621-627 (1971); Delamaire, M. et al. *Diabetic Med* 14, 29-34 (1997)] and phagocytosis [Bagdade, J. D. et al. *Diabetes* 23, 9-15 (1974)] resulting in an increased susceptibility to bacterial infections [Shah, B. R. & Hux, J. E. *Diabetes Care* 26, 510-513 (2003)]. A comprehensive phenotyping of neutrophil functions in T2DM patients therefore enables early and direct characterization of immune health for timely therapeutic interventions. However, it is non-trivial to isolate neutrophils in their native state from peripheral blood as conventional neutrophil isolation methods are laborious and prone to cell activation [Fukuda, S. & Schmid-Schönbein, G. W. *J. Leukoc. Biol.* 72, 133-139 (2002)], which can be greatly minimized with antibodies-free neutrophil isolation methods [Dorward, D. A. et al. *J. Leukoc. Biol.* 94, 193-202 (2013)]. Critically, there are currently no point-of-care (POC) technologies enabling the quantification of neutrophil function related to a low grade inflammatory state. This advocates a strong clinical need to develop novel technologies for rapid, label-free neutrophil sorting and functional phenotyping to better characterize the inflammatory status of T2DM patients.

With advances in microfabrication, microfluidics provides an exciting tool box for point-of-care diagnostics and biomedical research with its low consumption of sample and reagents, device miniaturization, and high throughput single-cell analysis [Sackmann, E. K., Fulton, A. L. & Beebe, D. J. *Nature* 507, 181-189 (2014)]. Several microfluidics technologies have been developed for neutrophil sorting [Kotz, K. T. et al. *Nat. Med.* 16, 1042-1047 (2010); Sackmann, E. K.-H. et al. *Proc. Natl. Acad. Sci. U.S.A* 111, 5813-5818 (2014); Bose, S. et al. *Sci. Rep.* 3, 2329 (2013)] and are used to study inflammatory responses in patients with severe trauma and burn injury, as well as asthma. These devices achieve neutrophil purification based on antibodies binding (CD66b and P-selectin), and subsequent characterizations are performed on chip as the sorted neutrophils are attached inside the microchannel. This inherently limits downstream applications including in vitro cell culture assays and flow cytometry analysis since it is challenging to recover the sorted neutrophils from the device. Noteworthy, no published reports to date have applied microfluidics for neutrophil functional phenotyping in T2DM patients, which would be invaluable in studying the association among alterations of cardiovascular risk factors, abnormal leukocyte phenotypes and the accompanied endothelial dysfunction.

Dean Flow Fractionation (DFF) for is known in the art for size-based separation of diseased cells including circulating tumor cells (CTCs) and microorganisms [Hou, H. W. et al., *Sci. Rep.* 3 (2013); Hou, H. W. et al., *Lab Chip* 15, 2297-2307 (2015)].

Hence, there is need in the art for methods and devices to gently purify blood components, specifically neutrophils, which allow further testing of the purified components, for example to apply them in diabetes assays.

SUMMARY OF THE INVENTION

It is an object of the present invention to meet the above need by providing a method for separating blood cells. Surprisingly, the present inventors have found that the use of Dean Flow Fractionation (DFF) allows the fractionation of blood samples and the purification of blood components or microparticles, such as bacteria, occurring in the blood. The present inventors found a combination of different parameters of the Dean Flow Fractionation that allows purification of neutrophils without applying a centrifugation step and/or a labeling step using a marker molecule. Using such method, neutrophils are purified gently (in their native state) and fast compared to methods that use centrifugation and/or labeling steps.

The above described method to purify neutrophils in the native state is highly qualified to be coupled with a method for diagnosing diabetes, which involves further investigation of neutrophils by determining their rolling speed, the neutrophil circularity (NC) index and/or the expression of markers, such as intracellular reactive oxygen species (ROS), CD11b or PSGL-1.

In a first aspect, the present invention is thus directed to a method for separating blood cells comprising the steps of: (a) lysing red blood cells of a blood sample and diluting said sample; (b) providing a microfluidic device comprising a spiral-shaped flow channel having at least a first end and a second end, wherein said flow channel has two inlet ports at or near said first end and at least two outlet ports at or near said second end, wherein one of the two inlet ports is located at the inner wall of the spiral-shaped flow channel and the other inlet port is located at the outer wall of the spiral-shaped flow channel and at least one of the outlet ports is connected to a container allowing the storage of blood cells; (c) introducing the sample of step (a) into the inlet port located at the outer wall of the spiral-shaped flow channel and introducing a sheath fluid into the inlet port located at the inner wall of the spiral-shaped flow channel; (d) driving said sample and the sheath fluid through the spiral-shaped flow channel; and (e) recovering the blood cells in the at least one container connected to the at least one outlet port.

In various embodiments of the invention, the method of the invention does not comprise (a) a centrifugation step; and/or (b) a labeling step, wherein at least one type of blood cells is labeled with a marker molecule.

The scope of the present invention also encompasses various embodiments wherein the sample is a finger prick sample or a sample generated from venipuncture.

In still further various embodiments of the invention, the at least two outlet ports are at least four outlet ports. In other various embodiments, the Reynolds number (Re) of the sample flowing through the spiral-shaped flow channel is 50-100.

Also encompassed by the scope of the present invention is that the spiral-shaped flow channel (a) comprises or consists of polydimethylsiloxane (PDMS); (b) has a width of 300-600 µm, preferably 500 µm; (c) has a height of 110-130 µm, preferably 115 µm; and/or (d) has a total length of 7-13 cm, preferably 10 cm.

In various embodiments, the spiral-shaped flow channel gradually expands to a width of 800-1200 µm at the furcation of the outlet ports. In preferred embodiments, the expanded width is 1000 µm.

In further various embodiments of the invention, the first outlet port covers the width 0-100 µm, the second outlet port covers the width 101-250 µm, the third outlet port covers the width 251-650 µm and the fourth outlet port covers the width 651-1000 µm of the flow channel defined from the inner wall towards the outer wall.

Also encompassed are embodiments, wherein the blood cells comprise neutrophils, monocytes and lymphocytes, platelets and red blood cells. In more preferred embodiments, neutrophils and monocytes are recovered by the second outlet port and/or lymphocytes are recovered by the third outlet port.

In various embodiments, (a) the flow rate of the sheath fluid is at least 5-fold, preferably at least 10-fold, higher than the flow rate of the diluted sample; and/or (b) the flow rate of the diluted sample is 120-130 µL/min.

In still further embodiments, (a) the blood cells are recovered in a buffer; and/or (b) the blood sample is diluted at least 1:5 with a buffer.

In a further aspect, the present invention relates to a method for diagnosing diabetes or an inflammatory disease in a subject comprising: (a) providing a blood sample of said subject and isolating the neutrophils; (b) determining (I) whether the isolated neutrophils of the sample of said subject have an increased average rolling speed compared to isolated neutrophils of a comparable control sample of at least one healthy individual, wherein an increased rolling speed is indicative for diabetes or the inflammatory disease; (II) whether the isolated neutrophils of the sample of said subject have a decreased neutrophil circularity (NC) index compared to isolated neutrophils of a comparable control sample of at least one healthy individual, wherein a decreased neutrophil circularity (NC) index is indicative for diabetes or the inflammatory disease, or (III) whether the isolated neutrophils of the sample of said subject have an increased expression of intracellular reactive oxygen species (ROS) or CD11b or a decreased expression of PSGL-1 compared to isolated neutrophils of a comparable control sample of at least one healthy individual, wherein an increased expression of intracellular reactive oxygen species (ROS) or CD11b or a decreased expression of PSGL-1 is indicative for diabetes or the inflammatory disease.

In various embodiments of the invention, the neutrophils are isolated according to the method for separating blood cells from serum or plasma of the invention.

The scope of the present invention also encompasses various embodiments wherein the diabetes is type 2 diabetes mellitus (T2DM).

In still further various embodiments of the invention relating to the determination of the neutrophil rolling speed, the increased average rolling speed is at least 5.30 µm/sec. In various other embodiments, the rolling speed is determined in a channel coated with E-selectin.

Also encompassed by the scope of the present invention is, in embodiments relating to the determination of the neutrophil circularity (NC) index, that a decreased neutrophil circularity (NC) index is defined as less than 76% of the tested neutrophils having a neutrophil circularity (NC) of at least 0.85.

In various embodiments relating to the expression of intracellular reactive oxygen species (ROS), CD11b and PSGL-1, (a) the intracellular reactive oxygen species (ROS) or CD11b expression in the isolated neutrophils of the sample of said subject is at least 10% increased compared to the expression in the comparable control sample; and/or (b) the PSGL-1 expression in the isolated neutrophils of the sample of said subject is at least 10% decreased compared to the expression in the comparable control sample.

In a still further aspect of the invention, the scope encompasses a microfluidic device comprising a spiral-shaped flow channel having at least a first end and a second end, wherein said flow channel has two inlet ports at or near said first end and at least two outlet ports at or near said second end, wherein one of the two inlet ports is located at the inner wall of the spiral-shaped flow channel and the other inlet port is located at the outer wall of the spiral-shaped flow channel and at least one of the outlet ports is connected to a container allowing the storage of blood cells; wherein the flow channel has a height of 110-130 µm, preferably 115 µm.

In various embodiments of the device, the at least two outlet ports are at least four outlet ports.

The scope of the present invention also encompasses various embodiments wherein the spiral-shaped flow channel gradually expands to a width of 800-1200 µm at the furcation of the outlet ports. In preferred embodiments, the spiral-shaped flow channel gradually expands to a width of 800-1200 µm at the furcation of the outlet ports. In more preferred embodiments, the expanded width is 1000 µm. In still more preferred embodiments, the first outlet port covers 5-30%, preferably 20%, of the width of the flow channel and the second outlet port covers 70-95% of the width of the flow channel, wherein the first outlet port is located at the inner wall and the second outlet port is located at the outer wall.

Also encompassed by the scope of the present invention is that in various embodiments the spiral-shaped flow channel (a) comprises or consists of polydimethylsiloxane (PDMS); (b) has a total length of 7-13 cm, preferably 10 cm; and/or (c) has a width of 400-600 µm, preferably 500 µm.

In preferred embodiments of the device, the at least two outlet ports are two outlet ports. In more preferred embodiments of the above defined two outlet ports device, the first outlet port covers the width 0-50 µm and the second outlet port covers the width 51-300 µm of the flow channel defined from the inner wall towards the outer wall. In various embodiments of the above defined two outlet ports device, the spiral-shaped flow channel (a) comprises or consists of polydimethylsiloxane (PDMS); (b) has a total length of 5-10 cm, preferably 6.5 cm; (c) has a width of 200-400 µm, preferably 300 µm; and/or (d) has a height of 30-90 µm, preferably 60 µm.

BRIEF DESCRIPTION OF THE DRAWINGS

The invention will be better understood with reference to the detailed description when considered in conjunction with the non-limiting examples and the accompanying drawings.

FIG. 7 shows a table with characteristics of healthy and T2DM patients examined in studies of the present application.

FIG. 8 shows a table depicting the dependence of the ratio of purified cell types (cell size dependent) and channel height of the flow channel.

DETAILED DESCRIPTION OF THE INVENTION

Figure 1:
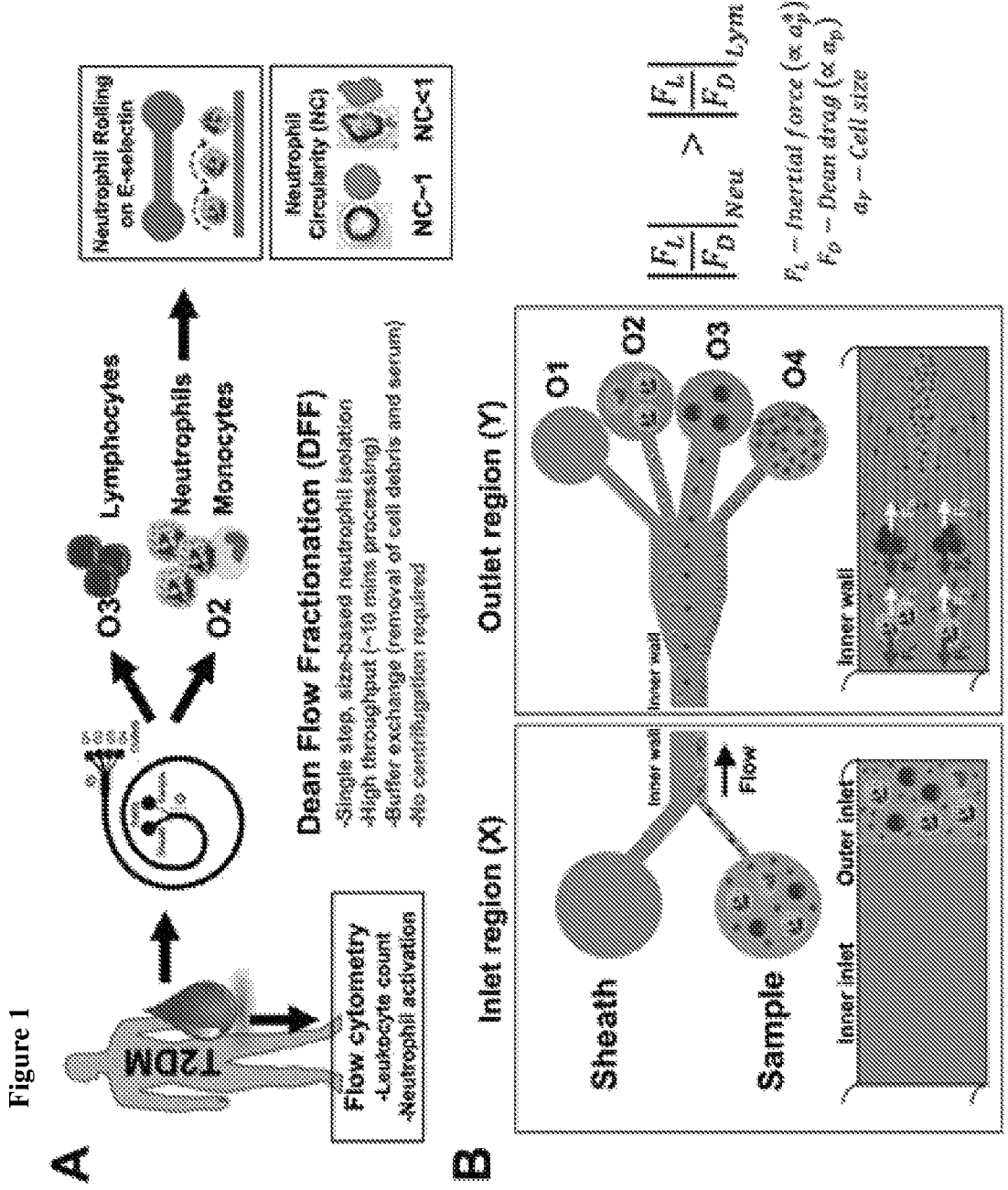
FIG. 1 shows a single step and label-free neutrophil sorting using Dean Flow Fractionation (DFF) microfluidic technology. (A) Experimental workflow for neutrophil isolation and phenotyping in T2DM patients. Blood samples are lysed and processed using the developed 2-inlet, 4-outlet spiral microdevice for efficient size-based neutrophil sorting. The purified neutrophils from outlet 2 are used for in vitro cell rolling assay in a microchannel functionalized with E-selectin, as well as shape measurement (neutrophil circularity). Leukocyte count and neutrophil activation level are determined by flow cytometry analysis. (B) Schematic illustration of DFF separation principle. Lysed blood sample and sheath fluid (1×PBS with 0.1% BSA) are pumped into the device inlets at different flow rates (1:10) to confine the sample flow at the channel outer wall. Under the influence of Dean vortices, small cellular constituents (platelets and lysed RBCs) and free haemoglobin migrate laterally towards inner wall and back to outer wall due to Dean drag forces ($F_D$ (yellow arrows)). Larger leukocytes experience additional strong inertial lift forces ($F_L$ (red arrows)) and focus near the inner wall at the outlet region to achieve continuous separation and buffer exchange of sorted leukocytes. Due to the strong dependence of $F_L$ and $F_D$ on cell size, larger neutrophils/monocytes (10-12 µm) focus closer to the inner wall and are sorted into outlet 2 while smaller lymphocytes (~7-8 µm) are collected at outlet 3. Outlet 4 is used for removal of platelets, lysed RBCs and free haemoglobin.

The present inventors surprisingly found that Dean Flow Fractionation (DFF) is qualified to separate blood components and/or microparticles (such as bacteria) present in blood. According to the components or microparticles of interest, the parameter settings of the microfluidic device need to be adapted for efficient and distinct purification. The present inventors found a method, which allows the separation of neutrophils from other blood components. Subsequently, these purified neutrophils can be used in further assays for diagnosing diabetes.

Therefore, in a first aspect, the present invention is thus directed to a method for separating blood cells comprising the steps of: (a) lysing red blood cells of a blood sample and diluting said sample; (b) providing a microfluidic device comprising a spiral-shaped flow channel having at least a first end and a second end, wherein said flow channel has two inlet ports at or near said first end and at least two outlet ports at or near said second end, wherein one of the two inlet ports is located at the inner wall of the spiral-shaped flow channel and the other inlet port is located at the outer wall of the spiral-shaped flow channel and at least one of the outlet ports is connected to a container allowing the storage of blood cells; (c) introducing the sample of step (a) into the inlet port located at the outer wall of the spiral-shaped flow channel and introducing a sheath fluid into the inlet port located at the inner wall of the spiral-shaped flow channel; (d) driving said sample and the sheath fluid through the spiral-shaped flow channel; and (e) recovering the blood cells in the at least one container connected to the at least one outlet port.

The microfluidic cell sorting technology termed Dean Flow Fractionation (DFF) is well-known for size-based separation of diseased cells [Hou, H. W. et al. *Sci. Rep.* 3 (2013); Hou, H. W. et al. *Lab Chip* 15, 2297-2307 (2015)]. DFF is an inertial microfluidics based sorting method which involves the lateral migration of particles or cells across streamlines to focus at distinct positions due to dominant inertial forces ($F_L$) at high flow rates (Reynolds number, Re ~50-100). In DFF systems, fluid flowing through a spiral microchannel experiences centrifugal acceleration directed radially outward, leading to the formation of two symmetrical counter-rotating Dean vortices at the top and bottom halves of the channel. The presence of Dean vortices in spiral microchannels imposes additional lateral Dean drag force ($F_D$) which offers superior separation resolution as both forces ($F_L$ and $F_D$) scale non-linearly with particle size and their superposition ($F_L/F_D$) determines the equilibrium position within the channel cross section (FIG. 1B).

The terms "separation", "separating", or "partially purifying", as interchangeably used herein, relate to one type of molecules, in particular a natural or non-natural component of a blood sample (preferably neutrophils and/or monocytes), that is at least 60% free, preferably 75% free, and most preferably 90% free from other components of a blood sample that are (naturally or non-naturally) occurring in this sample. These percentage values may relate to the weight or the molarity of the component of interest. For examples, this means if monocytes and neutrophils after separation are recovered together in one container but at least 60% of other components of the blood sample are not present in said container, the monocytes and neutrophils are separated from serum. In various embodiments, the recovered neutrophils and/or monocytes are separated from lymphocytes. This means that the neutrophils and/or monocytes are separated from at least 30%, 40%, 50%, 60%, 70%, 75%, 80%, 85%, 90%, 95% or 98% of lymphocytes that are naturally associated with these cells.

The term "blood cells", as used herein, is meant to include platelets, red blood cells and leukocytes (white blood cells). All white blood cells are nucleated, which distinguishes them from the anucleated red blood cells and platelets. Types of leukocytes can be classified in standard ways. Two pairs of broadest categories classify them either by structure (granulocytes or agranulocytes) or by cell lineage (myeloid cells or lymphoid cells). These broadest categories can be further divided into the five main types: neutrophils, eosinophils, basophils, lymphocytes, and monocytes. These types are distinguished by their physical and functional characteristics. Monocytes and neutrophils are phagocytic. Further subtype classification is well-known in the art.

"Sample" or "patient sample", as used herein, includes biological samples such as tissues and bodily fluids. "Bodily fluids" may include, but are not limited to, blood, serum, plasma, saliva, cerebral spinal fluid, pleural fluid, tears, lactal duct fluid, lymph, sputum, urine, amniotic fluid, and semen. A sample may include a bodily fluid that is "acellular". An "acellular bodily fluid" includes less than about 1% (w/w) whole cellular material. Plasma or serum are examples of acellular bodily fluids. A sample may include a specimen of natural or synthetic origin. "Plasma", as used herein, refers to acellular fluid found in blood. "Plasma" may be obtained from blood by removing whole cellular material from blood by methods known in the art (e.g., centrifugation, filtration, and the like). As used herein, "peripheral blood plasma" refers to plasma obtained from peripheral blood samples. "Serum", as used herein, includes the fraction of plasma obtained after plasma or blood is permitted to clot and the clotted fraction is removed. Thus, a serum sample is also acellular. In contrast, the term "whole blood", as used herein, means blood per se collected from a subject such as a human and containing unseparated blood cells. Further, a sample obtained by diluting the whole blood with an appropriate buffer or the like, and/or by adding an additive, such as an anticoagulant or a protease inhibitor, may be used as the whole blood sample. A whole blood sample comprises blood cells, such as platelets, red blood cells and leukocytes.

"Lysing", as used herein, is a rupturing of the red blood cells or their proteins to release the desired blood component or microparticle of interest, such as neutrophils and/or monocytes.

The term "dilution", as used herein, generally encompasses the ordinary meaning of that term, namely, the reduction in the amount of a particular subject material per unit volume of a fluid containing that material, through the addition of a second fluid, or diluent, to a first fluid which contains the subject material, e.g., soluble chemical component, or a suspension or emulsion of a partially insoluble material, whereby the resulting concentration of the subject material is reduced over that of the first fluid. In terms of the present invention, the diluent may take on a variety of forms, including aqueous or nonaqueous fluids and/or it may include additional material components, e.g., soluble chemical components or suspensions or emulsions of at least partially insoluble components. As alluded to above, the subject material may comprise virtually any composition, including chemical compounds, either soluble or as suspensions or emulsions, biological material, either soluble or as suspensions (e.g., cells) or emulsions, and the like. In various embodiments, the subject material is a blood sample as defined above and/or the diluent is a buffer, preferably a compatible with blood cells, such as phosphate-buffered saline (abbreviated PBS) and other well-known buffers. The ratio of the volume of the subject material to the volume of the diluent may be at least 1:0.5; 1:1; 1:2; 1:3; 1:4; 1:5; 1:6; 1:7; 1:8; 1:9; 1:10; 1:13; 1:15 or a range, such as 1:1 to 1:35; 1:5 to 1:30 or 1:10 to 1:20.

As used herein, the expression "flow channel" means a tubular passage for liquids. Preferably, the flow channel is spiral-shaped. As the spiral shape represent an asymmetrical shape, an inner and an outer wall can be defined (FIGS. 1, 10, 16 and 18). As used herein, the expression "microfluidic device" means a physical element that enables the control and manipulation of fluids that are geometrically constrained to a small, typically sub-millimeter scale. "Microfluidic device", as used herein, refers to a device that includes one or more microfluidic flow channels designed to carry, store, mix, react, and/or analyze liquid samples, typically in volumes of less than one milliliter. Representative examples of materials that can be used to make microfluidic devices include, but are not limited to, silicone rubber, glass, plastic, silicon and metals, preferably the microfluidic device is made of polydimethylsiloxane (PDMS).

The term "inlet port", as used herein, is defined as the end of the flow channel, which is first contacted with the diluted sample and the sheath fluid. On the contrary, the term "outlet port" refers to the end of the flow channel, which releases the fluidic material of the diluted sample and the sheath fluid from the microfluidic device.

The term "connected to a container", as used herein, relates to the transfer of a fluid recovered in the microfluidic device of the invention to a second storage unit. A "container", in the sense of the present invention, can be a unit whose only function is to store the recovered fluid, but also a device, which allows further purification, such as a column or a filter unit, or analysis of the recovered fluid. The devices used for analysis of the recovered fluid may comprise, but are not limited to FACS devices, mass spectrometry devices, microscopes, centrifuges, PCR thermocycler and a second flow channel comprising a coating, which can be used to carry out functional assays. In various embodiments, such coated channel comprises a E-selectin coating that allows to measure the rolling speed of neutrophils.

The term "sheath fluid", as used herein, refers to a variety of fluids, including aqueous or nonaqueous fluids and/or fluids that may include additional material components, e.g., soluble chemical components or suspensions or emulsions of at least partially insoluble components. Preferably, the sheath fluid is a buffer, preferably a compatible with blood cells, such as phosphate-buffered saline (abbreviated PBS) and other well-known buffers. The term "buffer", as used herein, means any compound or combination of compounds that control the pH of the environment in which they are dissolved or dispersed. Concerning the pH value, buffers diminish the effect of acids or basis added to the buffer solution. Buffers generally can be broken into two categories based upon their solubility. Both categories of buffer separately, or in combination, can be employed. "Water-soluble buffers" typically have a solubility in water of at least 1 gm in 100 ml, preferably at least 1 gm in 75 ml, and more preferably at least 1 gm in 30 ml. Examples of water-soluble buffers include, but are not limited to PBS, meglumine, sodium bicarbonate, sodium carbonate, sodium citrate, calcium gluconate, disodium hydrogen phosphate, dipotassium hydrogen phosphate, tripotassium phosphate, sodium tartarate, sodium acetate, calcium glycerophosphate, tromethamine, magnesium oxide or any combination of the foregoing. "Water-insoluble buffers" typically have a solubility in water less than 1 gm in 1,000 ml, preferably less than 1 gm in 5,000 ml, and more preferably less than 1 gm in 10,000 ml, Examples of water-insoluble buffers include, but are not limited to magnesium hydroxide, aluminum hydroxide, dihydroxy aluminum sodium carbonate, calcium carbonate, aluminum phosphate, aluminum carbonate, dihydroxy aluminum amino acetate, magnesium oxide, magnesium trisilicate, magnesium carbonate, and combinations of the foregoing. Buffer can also be supplemented with supporting agents, such as salts, detergents, BSA (bovine serum albumin) etc. Concentrations that can be used for each of the above recited buffers are well-known in the art.

The sample can be driven by the force of capillary attraction. Alternatively, the sample can be driven a pump, by electrical forces, or by other means for driving samples. Pumps include, but are not limited to, rotary (centrifugal) pumps; peristaltic pumps; and ultrasonic pumps. Electrical forces include, but are not limited to, electrohydrodynamic forces; electrokinetic forces, e.g., electrophoresis, electroosmosis; and surface tension driven, e.g., electrowetting, electrowetting on dielectric surface. Means for driving samples are discussed in greater detail by Nguyen et al., Erickson et al., Grover et al., Hunt et al. and Bersano-Begey et al. [Nguyen et al., *Fundamentals and Applications of Microfluidics*, Second Edition, ARTECH HOUSE, INC. (Norwood, Mass.: 2006), pages 255-309; Erickson et al., Introduction to Electrokinetic Transport in Microfluidic Systems, *Lab on a Chip Technology*, Volume 1: *Fabrication and Microfluidics*, edited by Herold et al., Caister Academic Press (Norfolk, UK: 2009), pages 231-248; Grover et al., Monolithic Membrane Valves and Pumps, *Lab on a Chip Technology, Volume 1: Fabrication and Microfluidics*, edited by Herold et al., Caister Academic Press (Norfolk, UK: 2009), pages 285-317; Hunt et al., Integrated Circuit/Microfluidic Chips for Dielectric Manipulation, *Lab on a Chip Technology, Volume 2: Biomolecular Separation and Analysis*, edited by Herold et al., Caister Academic Press (Norfolk, UK: 2009), pages 187-206, Bersano-Begey et al., Braille Microfluidics, *Lab on a Chip Technology, Volume 2: Biomolecular Separation and Analysis*, edited by Herold et al., Caister Academic Press (Norfolk, UK: 2009), pages 269-285]. Nguyen et al. discusses microvalves, micropumps, microflow sensors, microfilters and microseparators in detail. The chapters in Herold et al. discuss valves, pumps, and separation in detail.

The sample can be introduced to a flow channel of a microfluidic device by means of a syringe, by dipping the device into the sample, or other means. Other means for introducing a sample into a flow channel of a microfluidic device include microdispensers, e.g., droplet dispensers, such as, for example, injection nozzles; in-channel dispensers, e.g., metering dispensers. Means for introducing samples into a flow channel of a microfluidic device are discussed in greater detail by Nguyen et al. and Li et al. [Nguyen et al., *Fundamentals and Applications of Microfluidics*, Second Edition, ARTECH HOUSE, INC. (Norwood, Mass.: 2006), pages 395-417; Li et al., Injection Schemes for Microchip-based Analysis Systems, *Lab on a Chip Technology, Volume 1: Fabrication and Microfluidics*, edited by Herold et al., Caister Academic Press (Norfolk, UK: 2009), pages 385-403]. Nguyen et al. discusses microdispensers in detail. Li et al. discusses microdispensers in detail.

The term "recovering", as used herein, refers to the process of rendering a species such as a polypeptide or cell substantially free of naturally associated components by isolation, e.g., using cell and/or protein purification techniques well known in the art.

In various embodiments of the invention, the method of the invention does not comprise (a) a centrifugation step; and/or (b) a labeling step, wherein at least one type of blood cells is labeled with a marker molecule. The term "centrifugation step", as used herein, refers to the separation of cells from other components (e.g. non-cell components) of the cell sample provided by centrifugation. The centrifugal step may comprise one, more or all of the following aspects but is not limited to gradient separation, erythrocyte reduction, platelet removal and cell washing. The term "labeling", as used herein, denotes the attachment or incorporation of one or more detectable markers (or "labels") into a cell, protein and/or peptide used in the invention. The terms "marker molecule" or "detectable marker", as interchangeably used herein, refer to any compound that comprises one or more appropriate chemical substances or enzymes, which directly or indirectly generate a detectable compound or signal in a chemical, physical or enzymatic reaction. As used herein, the term is to be understood to include both the labels as such (i.e. the compound or moiety bound to the protein and/or peptide) as well as the labeling reagent (i.e. the compound or moiety prior to the binding with the peptide or protein). A label used in the present invention may be attached to an amino acid residue of a protein and/or peptide via a covalent or a non-covalent linkage. Typically, the linkage is a covalent linkage. The labels can be selected inter alia from isotopic labels, isobaric labels, enzyme labels, colored labels, fluorescent labels, chromogenic labels, luminescent labels, radioactive labels, haptens, biotin, metal complexes, metals, and colloidal gold, with isotonic labels and isobaric labels being particularly preferred. All these types of labels are well established in the art.

The scope of the present invention also encompasses various embodiments wherein the sample is a finger prick sample or a sample generated from venipuncture. "Finger prick sample", as used herein, is a sample of blood consisting of one drop collected from a finger (tip). Preferably, the sample is collected by a small fingertip lancet device capable of painlessly piercing the skin to cause fresh blood flow. Once a hanging droplet of blood is available on the finger a collector can be applied to the droplet and blood can be absorbed by the collector. The volume of the finger prick sample may range from 10-500 µL, preferably 50-300 µL and more preferably 80-150 µL.

In still further various embodiments of the invention, the at least two outlet ports are at least four outlet ports. In other various embodiments, the Reynolds number (Re) of the sample flowing through the spiral-shaped flow channel is 50-100.

As used herein, the expression "Reynolds number" means $\rho \upsilon L/\mu$; wherein $\rho$ represents density of a liquid; $\upsilon$ represents velocity of the liquid; L represents characteristic length of a flow channel and $\mu$ represents viscosity of the liquid.

Also encompassed by the scope of the present invention is that the spiral-shaped flow channel (a) comprises or consists of polydimethylsiloxane (PDMS); (b) has a width of 400-600 µm, preferably 500 µm; (c) has a height of 110-130 µm, preferably 115 µm; and/or (d) has a total length of 7-13 cm, preferably 10 cm.

Dimensions of microfluidic devices and the flow channels thereof, and the materials for constructing microfluidic devices and methods for constructing microfluidic devices are described by Nguyen et al., Tabeling, Armani et al., Tsao et al., Carlen et al., Cheung et al., Sun et al. and Waddell [Nguyen et al., *Fundamentals and Applications of Microfluidics*, Second Edition, ARTECH HOUSE, INC. (Norwood, Mass.: 2006), pages 55-115; Tabeling, *Introduction to Microfluidics*, Oxford University Press (Oxford, Great Britain: 2005), pages 244-295; Armani et al., Fabricating PDMS Microfluidic Channels Using a Vinyl Sign Plotter, *Lab on a Chip Technology, Volume 1: Fabrication and Microfluidics*, edited by Herold et al., Caister Academic Press (Norfolk, UK: 2009), pages 9-15; Tsao et al., Bonding Techniques for Thermoplastic Microfluidics, *Lab on a Chip Technology, Volume 1: Fabrication and Microfluidics*, edited by Herold et al., Caister Academic Press (Norfolk, UK: 2009), pages 45-63; Carlen et al., Silicon and Glass Micromachining, *Lab on a Chip Technology, Volume 1: Fabrication and Microfluidics*, edited by Herold et al., Caister Academic Press (Norfolk, UK: 2009), pages 83-114; Cheung et al., Microfluidics-based Lithography for Fabrication of Multi-Component Biocompatible Microstructures, *Lab on a Chip Technology, Volume 1: Fabrication and Microfluidics*, edited by Herold et al., Caister Academic Press (Norfolk, UK: 2009), pages 115-138; Sun et al., Laminated Object Manufacturing (LOM) Technology-Based Multi-Channel Lab-on-a-Chip for Enzymatic and Chemical Analysis, *Lab on a Chip Technology, Volume 1: Fabrication and Microfluidics*, edited by Herold et al., Caister Academic Press (Norfolk, UK: 2009), pages 161-172; Waddell, Laser Micromachining, Lab on a Chip Technology, Volume 1: *Fabrication and Microfluidics*, edited by Herold et al., Caister Academic Press (Norfolk, UK: 2009), pages 173-184].

In various embodiments, the spiral-shaped flow channel gradually expands to a width of 800-1200 µm at the furcation of the outlet ports. In preferred embodiments, the expanded width is 1000 µm.

As used herein, the term "furcated' means divided into branches. As used herein, the term "branch" means a limited part of a larger or more complex body, i.e., a smaller flow channel emerging from a primary flow channel or entering or re-entering a primary flow channel. As used herein, the term "primary flow channel" or "first flow channel" means a flow channel through which at least a majority of the sample flows.

In further various embodiments of the invention, the first outlet port covers the width 0-100 µm, the second outlet port covers the width 101-250 µm, the third outlet port covers the width 251-650 µm and the fourth outlet port covers the width 651-1000 µm of the flow channel defined from the inner wall towards the outer wall.

In alternative embodiments of the invention, the first outlet port covers 1-20% of the width of the flow channel, the second outlet port covers 10-20% of the width of the flow channel, the third outlet port covers 30-50% of the width of the flow channel and the fourth outlet port covers 25-45% of the width of the flow channel, wherein the order of the outlet ports 1-4 is defined from the inner wall towards the outer wall.

Also encompassed are embodiments, wherein the blood cells comprise neutrophils, monocytes and lymphocytes, platelets and red blood cells. In more preferred embodiments, neutrophils and monocytes are recovered by the second outlet port and/or lymphocytes are recovered by the third outlet port.

The term "leukocyte", as used herein, means mammalian cells of granulocytic and lymphocytic lineage. Examples of leukocyte cells are polymorphonuclear leukocytes, such as neutrophils, and mononuclear phagocytes, such as monocytes and macrophages, and lymphocytes.

The term "monocyte", as used herein, refers to a type of white blood cells that have two main functions in the immune system: (1) replenish resident macrophages and dendritic cells under normal states, and (2) in response to inflammation signals, monocytes can move quickly (approx. 8-12 hours) to sites of infection in the tissues and divide/differentiate into macrophages and dendritic cells to elicit an immune response. Half of them are stored in the spleen. Monocytes are usually identified in stained smears by their large bilobate nucleus. In addition to the expression of CD14, monocytes also show expression of one or more of the following surface markers 125I-WVH-1, 63D3, Adipophilin, CB12, CD11a, CD11b, CD15, CD54, Cd163, cytidine deaminase, Flt-1, and the like.

The term monocyte includes, without limitation both the classical monocyte and the non-classical pro-inflammatory monocyte, which are both present in human blood.

The term "the classical monocyte", as used herein, refers to a type of monocyte cell characterized by high level expression of the CD14 cell surface receptor (CD14++ monocyte) and the term "the non-classical pro-inflammatory monocyte", as used herein, refers to a cell with low level expression of CD14 and with additional co-expression of the CD16 receptor (CD14+CD16+ monocyte) which are characterized by producing high amounts of pro-inflammatory cytokines such as tumor necrosis factor and interleukin-12 in response to stimulation by microbial products. These cells develop from the CD14++ monocytes.

The term "macrophage", as used herein, refers to CD14+ positive cells derived from the differentiation of the monocytes characterized in that are phagocytes, acting in both non-specific defense (innate immunity) as well as to help initiate specific defense mechanisms (adaptive immunity) of vertebrate animals. Their role is to phagocytose (engulf and then digest) cellular debris and pathogens either as stationary or as mobile cells, and to stimulate lymphocytes and other immune cells to respond to the pathogen.

In addition to the expression of CD14, macrophages also show expression of one or more of the following surface markers: CD11b, F4/80 (mice)/EMR1 (human), Lysozyme M, MAC-1/MAC-3, 27E10, Carboxypeptidase M, Cathepsin K, CD163 and CD68. These markers can be determined by flow cytometry or immunohistochemical staining.

The term "myeloid dendritic cell", as used herein, refers to a population of dendritic cells which derive from monocytes and which include, without limitation, mDC-1 and mDC-2. In addition to the expression of CD14, myeloid dendritic cells also show expression of one or more of the following surface markers: ADAM19, BDCA-2, CDa, CD11c, CD21, CD86, CD208, Clusterin, Estrogen Receptor-alpha.

"Neutrophils", as used herein, mean mature white blood cells that arise from precursor cells such as myelocytes, metamyelocytes and band forms and that has a cytoplasm that is not acidophilic or basophilic like eosinophils or basophils. The term of "neutrophils" includes neutrophils and megaloblastic neutrophils that are caused because the lack of Vitamin B12 and or folate deficiency. Megaloblastic neutrophils may have also a hypersegmented nucleus. Neutrophils also cover neutrophil-like cells in animals including man. A specific example of neutrophil-like cells is the HL60 cells differentiated after treatment with dibutyric cyclic AMP. The term "neutrophil stimulating activity" means the activity of promoting the migration (sometimes referred to as "chemotaxis") and/or activation of neutrophils or neutrophil-like cells in animals including man. Migration covers infiltration of neutrophils or neutrophil-like cells into a tissue and their movement to a local site. Activation covers the production of active oxygen, secretion of degradative enzymes (e.g. β-HA), production of various cytokines and peroxides, as well as phagocytosis. These neutrophil stimulating activities can be assayed by measuring chemotactic activity of the neutrophil, release of active oxygen, and measuring the amount of β-HA secretion and/or the elevation of intracellular $Ca^{2+}$ concentration. When it is stated in this specification that a certain polypeptide "has neutrophil stimulating activity", the neutrophil stimulating activity of interest may be either the activity of promoting the migration of neutrophils or the activity of promoting the activation of neutrophils or both activities.

The term "lymphocyte cell" or "lymphocyte" as interchangeably used herein, refers to any one of a natural killer (NK) cell (usually involved in cell-mediated, cytotoxic innate immunity), a T cell (usually involved in cell-mediated, cytotoxic adaptive immunity), a B cell (usually involved in humoral, antibody-driven adaptive immunity), a plurality thereof and any combination thereof. Peripheral blood mononucleated (PBMC) cells, tumor-infiltrating-lymphocyte (TIL) cells and lymphokine-activated killer (LAK) cells (usually involved in tumor cells' killing) are also considered lymphocyte cells. Non-limiting examples of lymphocytes include cytotoxic lymphocytes (CTLs, $CD8^+$ or $CD4^+$), NK cells ($CD2^+$), and T helper cells ($CD4^+$).

In various embodiments, (a) the flow rate of the sheath fluid is at least 5-fold, preferably at least 10-fold, higher than the flow rate of the diluted sample; and/or (b) the flow rate of the diluted sample is 120-130 µL/min.

In still further embodiments, (a) the blood cells are recovered in a buffer; and/or (b) the blood sample is diluted at least 1:5 with a buffer.

"At least one", as used herein, relates to one or more, in particular 1, 2, 3, 4, 5, 6, 7, 8, 9, 10 or more.

In a further aspect, the present invention relates to a method for diagnosing diabetes or an inflammatory disease in a subject comprising: (a) providing a blood sample of said subject and isolating the neutrophils; (b) determining (I) whether the isolated neutrophils of the sample of said subject have an increased average rolling speed compared to isolated neutrophils of a comparable control sample of at least one healthy individual, wherein an increased rolling speed is indicative for diabetes or the inflammatory disease; (II) whether the isolated neutrophils of the sample of said subject have a decreased neutrophil circularity (NC) index compared to isolated neutrophils of a comparable control sample of at least one healthy individual, wherein a decreased neutrophil circularity (NC) index is indicative for diabetes or the inflammatory disease, or (III) whether the isolated neutrophils of the sample of said subject have an increased expression of intracellular reactive oxygen species (ROS) or CD11b or a decreased expression of PSGL-1 compared to isolated neutrophils of a comparable control sample of at least one healthy individual, wherein an increased expression of intracellular reactive oxygen species (ROS) or CD11b or a decreased expression of PSGL-1 is indicative for diabetes or the inflammatory disease.

The terms "diagnosing" and "diagnosis", as used herein, refers to methods by which a skilled person can estimate and even determine whether or not a subject is suffering from a given disease, disorder or condition. The skilled person makes the diagnosis on the basis of one or more diagnostic indicators (as recited above), the amount (including presence or absence) of which is indicator for the presence, severity, or absence of the condition.

The term "subject", as used herein, refers to an individual, plant, or animal, such as a human beings, a non-human primate (e.g. chimpanzees and other apes and monkey species), a farm animal (e.g. birds, fish, cattle, sheep, pigs, goats, and horses), a domestic mammal (e.g. dogs and cats), or a laboratory animal (e.g. rodents, such as mice, rats and guinea pigs). The term does not denote a particular age or sex. The term "subject" encompasses an embryo and a fetus. The term subject may be interchangeably used with the term patient in the context of the present invention.

"Diabetes", as used herein, refers to diabetes mellitus and includes type 1, type 2, and type 3 (also referred to as type 1.5) unless otherwise indicated. "Diabetes" corresponds to a fasting plasma glucose concentration greater than or equal to 126 mg/dl (6.9 mmol/1), or a plasma glucose concentration greater than or equal to 200 mg/dl (11.1 mmol/1) two hours after ingestion of a 75 g oral glucose load. Preferably, the diabetes is type 2 diabetes. The term "type 2 diabetes", as used herein, refers to a disease characterized by an inappropriate increase in blood glucose levels. The chronic hyperglycemia of diabetes is associated with long-term damage, dysfunction, and failure of different organs leading to a variety of complications such as retinopathy, nephropathy, and peripheral neuropathy. Type 2 diabetes is caused by insulin resistance in peripheral tissues (principally skeletal muscle, adipose tissue, and liver) and inappropriate compensatory insulin secretion response, due to the combination of decreased β-cell mass and function. In addition to increasing glucose concentration, faulty insulin action frequently translates into an increase in cholesterol or triglyceride levels.

"Inflammatory disease", as used herein, refers to a disease or condition characterized by inflammation. Inflammation encompasses the first response of the immune system to infection or irritation, and is sometimes referred to as the innate cascade. Inflammation typically is characterized by one or more of the following symptoms: redness, heat, swelling, pain, and dysfunction of the organs involved. "Treatment", as used herein, encompasses prevention of a disease or its progression, reduction of one or more symptoms (e.g., pain) associated with a disease or condition, and/or amelioration or curing of the underlying disease state or condition.

Examples of inflammatory diseases treatable as described herein include without limitation transplant rejection; chronic inflammatory disorders of the joints, such as arthritis, rheumatoid arthritis, juvenile idiopathic arthritis, ankylosing spondylitis, psoriatic arthritis, osteoarthritis and bone diseases associated with increased bone resorption; inflammatory bowel diseases, such as ileitis, ulcerative colitis, Barrett's syndrome, and Crohn's disease; inflammatory lung disorders, such as asthma, adult respiratory distress syndrome (ARDS), chronic obstructive pulmonary disease (COPD) or chronic obstructive airway disease; inflammatory disorders of the eye, such as corneal dystrophy, trachoma, onchocerciasis, uveitis, sympathetic ophthalmitis and endophthalmitis; chronic inflammatory disorders of the gum, such as gingivitis and periodontitis; tuberculosis; leprosy; inflammatory diseases of the kidney, such as uremic complications, glomerulonephritis and nephrosis; inflammatory diseases of the liver, such as viral hepatitis and autoimmune hepatitis; inflammatory disorders of the skin, such as sclerodermatitis, psoriasis, erythema, eczema, or contact dermatitis; inflammatory diseases of the central nervous system, such as stroke, chronic demyelinating diseases of the nervous system, multiple sclerosis, AIDS-related neurodegeneration and Alzheimer's disease, infectious meningitis, encephalomyelitis, Parkinson's disease, Huntington's disease, amyotrophic lateral sclerosis and viral or autoimmune encephalitis; autoimmune diseases, such as diabetes mellitus, immune-complex vasculitis, systemic lupus erythematosus (SLE); inflammatory diseases of the heart, such as cardiomyopathy, ischemic heart disease, hypercholesterolemia, and atherosclerosis; as well as inflammation resulting from various diseases such as preeclampsia, chronic liver failure, brain and spinal cord trauma, and cancer. Inflammatory diseases treatable as described herein further include systemic inflammations of the body. Examples of systemic inflammation include but are not limited to gram-positive or gram negative shock, sepsis, septic shock, hemorrhagic or anaphylactic shock, and systemic inflammatory response syndrome. Further examples of inflammatory disease include circulatory shock, hemorrhagic shock and cardiogenic shock.

The term "determining", as used herein, generally refers to the analysis or measurement of a confined volume (e.g., droplet), for example, quantitatively or qualitatively, and/or the detection of the presence, absence, or amount of a species, property, or condition within a confined volume.

Cells referred to herein as "isolated" are cells separated from other cells and other cellular components of their source of origin (e.g., as it exists in cells or in an in vitro or synthetic expression system), and may have undergone further processing. "Isolated", as used herein, refers to cells that are at least 60% free, preferably 75% free, and most preferably 90% free from other components with which they are naturally associated. This percentage value may relate to the weight or the number/molarity. "Isolated" cells include cells obtained by methods described herein, similar methods or other suitable methods, including essentially pure cells. "Isolating", as used herein, is defined as the process of releasing and obtaining a single constituent, such as a defined macromolecular species, from a mixture of constituents, such as from a culture of recombinant cells. This is typically accomplished by means such as centrifugation, filtration with or without vacuum, filtration under positive pressure, distillation, evaporation or a combination thereof. Isolating may or may not be accompanied by purifying during which the chemical, chiral or chemical and chiral purity of the isolate is increased. Purifying is typically conducted by means such as crystallization, distillation, extraction, filtration through acidic, basic or neutral alumina, filtration through acidic, basic or neutral charcoal, column chromatography on a column packed with a chiral stationary phase, filtration through a porous paper, plastic or glass barrier, column chromatography on silica gel, ion exchange chromatography, recrystallization, normal-phase high performance liquid chromatography, reverse-phase high performance liquid chromatography, trituration and the like.

The term "control sample", as used herein, refers to any clinically relevant comparative sample, including, for example, a sample from a healthy subject not afflicted with cancer or other disease, a sample from a subject having a less severe or slower progress of a given disease than the subject to be assessed, a sample from a subject having some other type of disease, a sample from a subject prior to treatment, a sample of non-diseased tissue (e.g., non-tumor tissue), a sample from the same origin and close to the disease site, and the like. A control sample may include a sample derived from one or more subjects. A control sample may also be a sample made at an earlier time point from the subject to be assessed. For example, the control sample could be a sample taken from the subject to be assessed before the onset of the disease, at an earlier stage of disease, or before the administration of treatment or of a portion of treatment. A control sample can be a purified sample, a cell, a chemical compound, protein, and/or nucleic acid. Such control samples can be further supplement with additional agents.

It will be appreciated that the term "healthy", as used herein, is relative to a specified disease, or disease factor, or disease criterion, as the term "healthy" cannot be defined to correspond to any absolute evaluation or status. Thus, an individual defined as healthy with reference to any specified disease or disease criterion, can in fact be diagnosed with any other one or more disease, or exhibit any other one or more disease criterion.

Leukocytes use the blood as a transport medium to reach the tissues of the body. Leukocyte extravasation is divided into four steps: chemoattraction, rolling adhesion, tight adhesion and transmigration. During rolling adhesion, carbohydrate ligands on the circulating leukocytes bind to selectin molecules on the inner wall of the vessel, with marginal affinity. This causes the leukocytes to slow down and begin rolling along the inner surface of the vessel wall. During this rolling motion, transitory bonds are formed and broken between selectins and their ligands. This rolling motion can be measured by determining the distance that is covered by the leukocytes in a given time frame. The term "rolling speed", as used herein, refers to this relation of covered distance and time. During diabetes the rolling speed of leukocytes is increased compared to the speed of leukocytes in healthy individuals. In preferred embodiments, a rolling speed of at least 4.5, 5.0, 5.3, 5.5, 6.0, 6.5 or 7.0 µm/sec is indicative for diabetes.

The term "neutrophil circularity (NC) index", as used herein, refers to a system that allows quantification of the morphology of leukocytes. To determine the neutrophil circularity index images of neutrophils are analyzed to determine cell circularity using the image analysis software, for example ImageJ version 1.33 (National Institutes of Health, Bethesda, Md.). Circularity [$(4\Pi^*area)/perimeter^2$] of the cell approaches 1.0 for a perfect circle; lower values reflect a progressively elongated ellipse. Methods and software to quantify the circularity of neutrophils are well-known in the art. In preferred embodiments, a decreased neutrophil circularity (NC) index is defined as less than 60%, 65% 70%, 73%, 76%, 78% or 80% of the tested neutrophils having a neutrophil circularity (NC) of at least 0.85.

The term "expressed" or "expression", as used herein, refers to the transcription from a gene to give an RNA nucleic acid molecule at least complementary in part to a region of one of the two nucleic acid strands of the gene. The term "expressed" or "expression", as used herein, also refers to the translation from said RNA nucleic acid molecule to give a protein or polypeptide or a portion thereof.

The term "reactive oxygen species (ROS), as used herein, relates to chemically reactive molecules containing oxygen. Examples include peroxides, superoxide, hydroxyl radical, and singlet oxygen. In a biological context, ROS are formed as a natural byproduct of the normal metabolism of oxygen and have important roles in cell signaling and homeostasis. However, during times of environmental stress (e.g., UV or heat exposure) or pathogenesis, ROS levels can increase dramatically.

Integrin alpha M (ITGAM) is one protein subunit that forms the heterodimeric integrin alpha-M beta-2 ($\alpha_M\beta_2$) molecule, also known as macrophage-1 antigen (Mac-1) or complement receptor 3 (CR3). ITGAM is also known as CR3A, and cluster of differentiation molecule 11B (CD11B). The second chain of $\alpha_M\beta_2$ is the common integrin $\beta_2$ subunit known as CD18, and integrin $\alpha_M\beta_2$ thus belongs to the $\beta_2$ subfamily (or leukocyte) integrins.

Selectin P ligand, also known as PSGL-1, SELPLG or CD162 (cluster of differentiation 162), is a human gene. SELPLG is the high affinity counter-receptor for P-selectin on myeloid cells and stimulated T lymphocytes. As such, it plays a critical role in the tethering of these cells to activated platelets or endothelia expressing P-selectin. P-selectin glycoprotein ligand-1 is a glycoprotein found on white blood cells and endothelial cells that binds to P-selectin (P stands for platelet), which is one of a family of selectins that includes E-selectin (endothelial) and L-selectin (leukocyte). Selectins are part of the broader family of cell adhesion molecules. PSGL-1 can bind to all three members of the family but binds best (with the highest affinity) to P-selectin.

In preferred embodiments, the expression level of intracellular reactive oxygen species (ROS) or CD11b in neutrophils derived from a patient having diabetes is at least 5%, 8%, 10%, 15%, 20%, 25%, 30%, 40%, 50% or 100% increased compared to the level in a healthy patient. In alternative preferred embodiments, the expression level of PSGL-1 in neutrophils derived from a patient having diabetes is at least 5%, 8%, 10%, 15%, 20%, 25%, 30%, 40%, 50% or 80% decreased compared to the level in a healthy patient.

In various embodiments of the invention, the neutrophils are isolated according to the method for separating blood cells from serum or plasma of the invention.

The scope of the present invention also encompasses various embodiments wherein the diabetes is type 2 diabetes mellitus (T2DM).

In still further various embodiments of the invention relating to the determination of the neutrophil rolling speed, the increased average rolling speed is at least 5.30 µm/sec. In various other embodiments, the rolling speed is determined in a channel coated with E-selectin.

E-selectin, also known as CD62 antigen-like family member E (CD62E), endothelial-leukocyte adhesion molecule 1 (ELAM-1), or leukocyte-endothelial cell adhesion molecule 2 (LECAM2), is a cell adhesion molecule expressed only on endothelial cells activated by cytokines. Like other selectins, it plays an important part in inflammation. In humans, E-selectin is encoded by the SELE gene.

Also encompassed by the scope of the present invention is, in embodiments relating to the determination of the neutrophil circularity (NC) index, a decreased neutrophil circularity (NC) index is defined as less than 76% of the tested neutrophils having a neutrophil circularity (NC) of at least 0.85.

In various embodiments relating to the expression of intracellular reactive oxygen species (ROS), CD11b and PSGL-1, (a) the intracellular reactive oxygen species (ROS) or CD11b expression in the isolated neutrophils of the sample of said subject is at least 10% increased compared to the expression in the comparable control sample; and/or (b) the PSGL-1 expression in the isolated neutrophils of the sample of said subject is at least 10% decreased compared to the expression in the comparable control sample.

In a still further aspect of the invention, the scope encompasses a microfluidic device comprising a spiral-shaped flow channel having at least a first end and a second end, wherein said flow channel has two inlet ports at or near said first end and at least two outlet ports at or near said second end, wherein one of the two inlet ports is located at the inner wall of the spiral-shaped flow channel and the other inlet port is located at the outer wall of the spiral-shaped flow channel and at least one of the outlet ports is connected to a container allowing the storage of blood cells; wherein the flow channel has a height of 110-130 µm, preferably 115 µm.

In various embodiments of the device, the at least two outlet ports are at least four outlet ports.

The scope of the present invention also encompasses various embodiments wherein the spiral-shaped flow channel gradually expands to a width of 800-1200 µm at the furcation of the outlet ports. In preferred embodiments, the spiral-shaped flow channel gradually expands to a width of 800-1200 µm at the furcation of the outlet ports. In more preferred embodiments, the expanded width is 1000 µm. In still more preferred embodiments, the first outlet port covers the width 0-100 µm, the second outlet port covers the width 101-250 µm, the third outlet port covers the width 251-650 µm and the fourth outlet port covers the width 651-1000 µm of the flow channel defined from the inner wall towards the outer wall.

Also encompassed by the scope of the present invention is that in various embodiments the spiral-shaped flow channel (a) comprises or consists of polydimethylsiloxane (PDMS); (b) has a total length of 7-13 cm, preferably 10 cm; and/or (c) has a width of 400-600 µm, preferably 500 µm.

In preferred embodiments of the device, the at least two outlet ports are two outlet ports. In more preferred embodiments of the above defined two outlet ports device, the first outlet port covers 5-30%, preferably 20%, of the width of the flow channel and the second outlet port covers 70-95% of the width of the flow channel, wherein the first outlet port is located at the inner wall and the second outlet port is located at the outer wall. In various embodiments of the above defined two outlet ports device, the spiral-shaped flow channel (a) comprises or consists of polydimethylsiloxane (PDMS); (b) has a total length of 5-10 cm, preferably 6.5 cm; (c) has a width of 200-400 µm, preferably 300 µm; and/or (d) has a height of 30-90 µm, preferably 60 µm.

All preferred embodiments described for the method of separation also apply to the microfluidic device of the invention.

In preferred embodiments, both method of the invention (1. method for separating blood cells and 2. method for diagnosing diabetes) are coupled. In this case, the neutrophils required for the diagnosis of diabetes are purified and generated according to the method for separating blood cells as described herein. Accordingly, to put such coupled method into practice the two devices that allow to perform the above described steps can be interconnected. Thus, a microfluidic device of the invention can be directly linked with a second microfluidic flow channel that is coated at its inner wall with E-selectin. Using the second flow channel the rolling speed of neutrophils can be determined as described herein. Thus, one or more outlet ports of the microfluidic device of the invention or its containers can be connected with the E-selectin coated flow channel to purify neutrophils from a sample and directly analyze their rolling speed to constitute a diabetes diagnosis for the tested patient.

In another aspect, the present invention also relates to a microfluidic flow channel, wherein its inner wall is coated with E-selectin. Such channel may have a length of at least 0.1 cm. Preferably, the channel has a length of 0.5-2 cm. The width may be at least 200 µm, preferably between 350-500 µm. The channel height may be at least 40 µm, preferably between 45-75 µm and more preferably the height is 60 µm. An example to determine the rolling speed by using an E-selectin coated channel is given below. Briefly, a straight microchannel (1 cm length by 400 µm width by 60 µm height) can be coated with E-selectin (50 µg/mL, Peprotech) for 1 h at 4° C. and blocked with 0.5% BSA in PBS for 30 min at room temperature. After blocking, the channel can be connected to a syringe loaded with 0.1% BSA in PBS to prime and wash away excess E-selectin in the channel. For rolling assay, $CaCl_2$ (20 µM, Sigma-Aldrich) can be added to the DFF-purified neutrophils to facilitate the calcium-dependent interactions of neutrophil binding and rolling on E-selectin. ~10-20 µL of DFF-purified neutrophils (~$10^6$ cells/mL) can be loaded at the inlet reservoir and the syringe can be set to withdraw at 2.6 µL/min (~2 dynecm$^{-2}$) to initiate neutrophil rolling. Phase contrast image can be captured for 30 s at the centre of the microchannel every 0.5 s interval (total of 61 frames) at 20× magnification using MetaMorph software (Molecular Devices). To induce inflammation and disease conditions, DFF-purified neutrophils can also be treated with tumor necrosis factor alpha (TNF-α, 10 ng/mL, Peprotech), PMA (2 nM, Sigma-Aldrich) or D-glucose (30 mM, Sigma-Aldrich) for 30 min at room temperature. The neutrophils can then be washed at 1000×g for 4 min and resuspended to a concentration of ~$10^6$ cells/mL with 20 µM $CaCl_2$ for rolling assay.

In a still further aspect, the present invention relates to a microfluidic device comprising a spiral-shaped flow channel as described above, wherein the flow channel may be made of PDMS and may have a width of 200-400 µm, preferably, 300 µm. The height may be 50-100 µm, preferably 60 µm. The total length of the channel may be 5-10 cm. The width of the first outlet port may be 0-50 µm and the width of the second outlet port may be 51-300 determined from the inner wall to the outer wall.

In a further aspect, the invention relates to a method of separating *S. aureus* and *E. coli*. This method uses the 2-outlet port device as described above.

In a still further aspect, the invention relates to a method of recovering microparticles from blood using the 2-outlet port device as described above.

EXAMPLES

Example 1: Microfluidic Neutrophil Purification and Phenotyping in Diabetes Mellitus A microfluidic cell sorting technology termed as Dean Flow Fractionation (DFF) has been developed for size-based separation of diseased cells including circulating tumor cells (CTCs) [Hou, H. W. et al. *Sci. Rep.* 3 (2013)] and microorganisms [Hou, H. W. et al. *Lab Chip* 15, 2297-2307 (2015)] from whole blood. Here, it was tested if the subtle cell size difference between leukocyte subtypes may be sufficient for separation by a 4-outlet DFF spiral device to purify neutrophils from lysed whole blood in a single-step manner (FIG. 1).

The DFF spiral device was fabricated in polydimethylsiloxane (PDMS) and consists of a two-inlet, four-outlet spiral microchannel (500 µm (w)×115 µm (h)) with a total length of ~10 cm. The channel height was fixed at 115 µm so that only the larger leukocytes (~8 to 12 µm, ap/h>0.07, where ap is particle size) can experience inertial focusing and equilibrate near the inner wall. Near the outlet region, the channel gradually expands to a larger width (1000 µm) at the furcation with 4 collection outlets of different widths (starting from inner wall: outlet 1 (O1): 100 µm, outlet 2 (O2): 150 µm, outlet 3 (O3): 400 µm, outlet 4 (O4): 350 µm). To purify neutrophils from whole blood, human whole blood was lysed with RBCs lysis buffer (1:10 volume) followed by quenching with 1× phosphate-buffered saline (PBS) supplemented with 0.5% bovine serum albumin (BSA) (1:2 volume). The diluted lysed blood sample was pumped into the outer inlet at 130 μLmin-1 and sheath fluid (1×PBS supplemented with 0.1% BSA) was pumped through the inner inlet at a higher flow rate (10×, 1300 μLmin-1) to confine the sample stream near the outer wall. As blood sample flows along the channel, cells undergo lateral migration towards the inner wall due to dominant FD. The smaller platelets and lysed RBCs (ap/h<0.05) recirculate back to outer wall to complete a Dean cycle (DC 1) while larger leukocytes (ap/h>0.07) experience additional inertial lift forces (FL) and focus near the inner wall. Due to cell size differences, the larger neutrophils/monocytes (10-12 μm, ap/h~0.9-0.1) experience stronger FL (towards inner wall direction) than lymphocytes (~7-8 μm, ap/h~0.07) and equilibrate closer to inner wall, resulting in leukocyte fractionation of neutrophils and lymphocytes into outlet 2 and 3, respectively (FIG. 1B). This facilitates efficient neutrophil purification as the sorted neutrophils are resuspended in sheath buffer during collection while the original lysed blood sample (platelets, lysed RBCs and free hemoglobin) is eluted at outlet 4.

To determine the optimal flow conditions for neutrophil purification, blood samples were lysed and washed with PBS to remove RBCs contaminants. The washed sample consisting mainly of leukocytes and platelets were then pumped into the spiral DFF device at different flow rates and eluents were collected from the 4 outlets for flow cytometry analysis. For leukocyte differential analysis, leukocytes were gated based on forward and side scatter signals, and stained with a cocktail of antibodies to identify neutrophils, monocytes and lymphocytes. As shown on FIG. 2A, the larger neutrophils and monocytes were efficiently sorted (>80%) into outlet 2 at a sample flow rate of 120-130 μLmin-1 and majority of the smaller lymphocytes (~95%) were separated into outlet 3. This was evident by high speed microscopic image showing inertial focusing of larger cells closer to the inner wall (FIG. 2B). The sorted leukocytes were also stained with Giemsa Wright stain to confirm neutrophil identity at outlet 2 and the cells were shown to well preserve their morphology post separation (FIG. 2C). As the flow rate increased above 130 μLmin-1, neutrophil recovery into outlet 2 was reduced while monocytes sorting remained unaffected. Hence, the optimal flow rate was set at 130 μLmin-1 for subsequent experiments to achieve high throughput neutrophil sorting with minimal lymphocytes contamination in outlet 2. This single-step procedure requires ~10 min to isolate neutrophils from a drop of fingerprick blood (~50 μL of whole blood; total lysed blood volume ~1-1.5 mL). Besides neutrophil purification, label-free fractionation of monocytes and lymphocytes was achieved using peripheral blood mononuclear cells (PBMCs) obtained from density gradient centrifugation (Fig. S2).

For point-of-care testing, it is important to minimize manual sample preparation to ensure results consistency. Next the effect of direct lysed blood processing (without centrifugation) was studied using DFF and similar neutrophil separation performance was demonstrated using lysed blood samples quenched with twice the saline volume. Neutrophils were focusing near the inner wall and clearly separated from the ghost RBCs (FIG. 2D) to achieve high neutrophil purity (~90%) in outlet 2 (FIG. 2E). Lastly, neutrophil CD66b expression and intracellular ROS level before and after DFF separation was characterized and it was shown that ROS level of sorted untreated neutrophils (obtained from healthy subjects) remained significantly lower than activated (PMA-treated) neutrophils. Consistent with previous studies [Wu, L. et al. *Anal. Chem.* 84, 9324-9331 (2012)], this indicates that the high flow conditions (~m/sec) within the spiral device have negligible effects on leukocyte activation and further validates the use of DFF neutrophil purification technology for processing blood samples from patients with T2DM or other states of dysmetabolism (e.g. cardiovascular diseases without diabetes).

To study neutrophil rolling phenotype on E-selectin, a straight microchannel (1 cm (l)×400 μm (w)×60 μm (h)) with recombinant human E-selectin (50 μg/mL) was coated to simulate flow conditions in post capillary venules (~1-10 dynecm$^{-2}$). DFF-sorted neutrophils were pumped into the channel at physiological shear conditions (2 dynecm$^{-2}$) and timelapse imaging was used to capture neutrophil rolling. A MATLAB tracking algorithm was developed to track neutrophil rolling trajectories and speed measurement for high throughput single cell analysis. As shown on FIG. 3A, healthy neutrophils exhibited steady rolling behavior in a straight path while rolling trajectories for tumor necrosis factor alpha (TNF-α)-activated neutrophils were discontinuous with "flipping" motions. Rolling speed of glucose-treated (30 mM) and TNF-α-activated (10 ng/mL) neutrophils were higher than healthy neutrophils (P<0.005) and PMA-treated (1 μM) neutrophils did not roll, but instead adhered firmly on E-selectin under flow (FIG. 3B). These differences in rolling phenotypes were further investigated by measuring neutrophil PSGL-1 expression, which is known to mediate leukocyte rolling on E-selectin, as well as CD11b, a Mac-1 integrin expressed on leukocytes that supports adhesion to E-selectin. PSGL-1 expression on neutrophils decreased with both glucose and TNF-α treatments and the downregulation was more significant for PMA-treated neutrophils which is consistent with previous report showing PSGL-1 shedding in activated leukocytes (FIG. 3C). Similarly, neutrophil CD11b level was upregulated for all treated conditions, with a higher increase in PMA-treated neutrophils (FIG. 3D). These results confirmed that altered surface expression of PSGL-1 and CD11b affect neutrophil rolling on E-selectin and suggest the use of cell rolling phenotype as a novel functional biomarker to assess neutrophil activation in diabetes patients.

Figure 4:
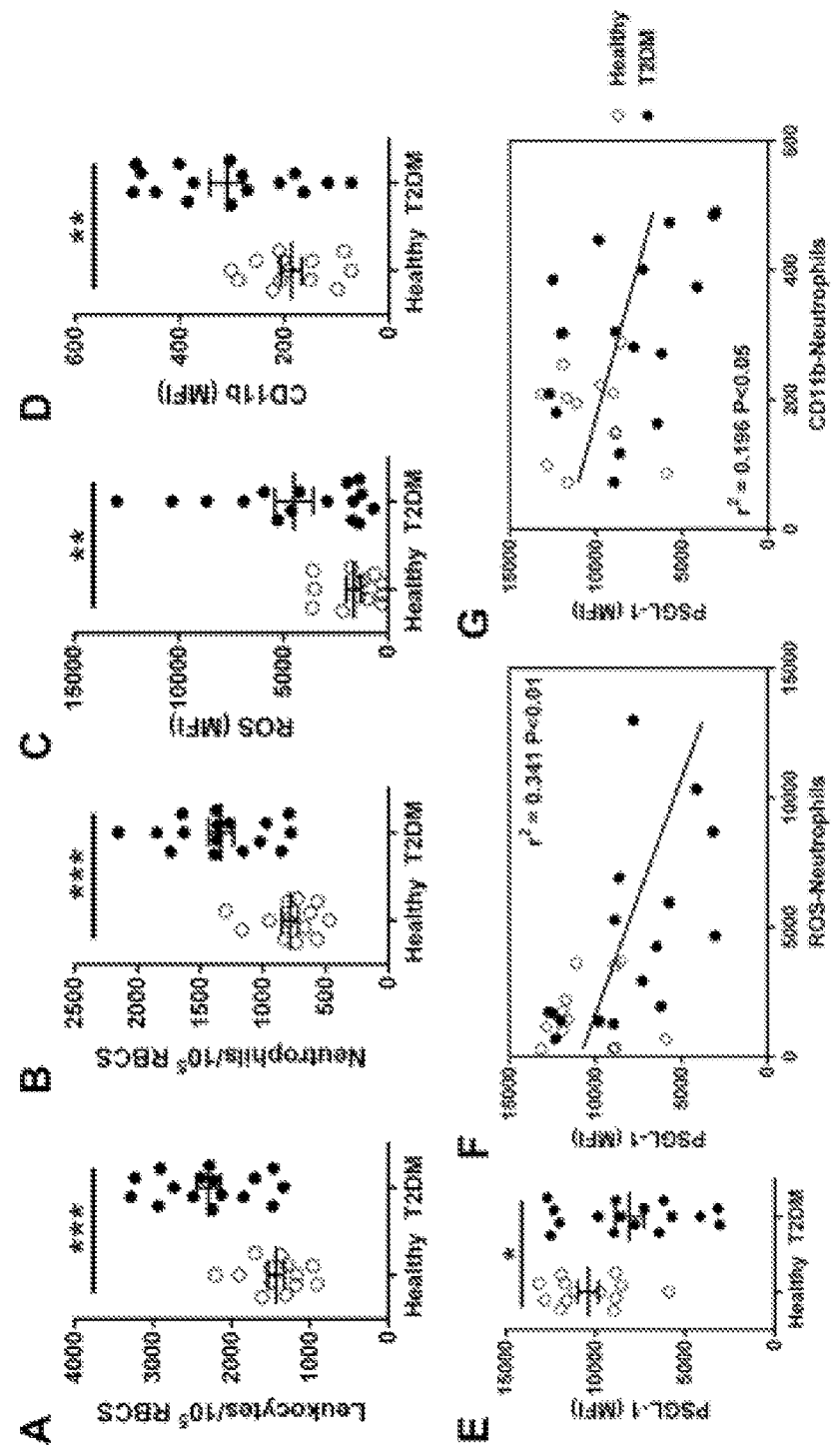
FIG. 4 shows neutrophil immunophenotyping in T2DM patients. Flow cytometry analysis on (A) leukocyte and (B) neutrophil count, and expression of (C) intracellular reactive oxygen species (ROS), (D) CD11b and (E) PSGL-1 on neutrophils from healthy (n=13) and T2DM patients (n=16). Data are presented as mean±s.e.m. *P<0.05, P<0.01 and *P<0.001. Correlation of neutrophil PSGL-1 level with (F) ROS and (G) CD11b expression.

As neutrophil dysfunctions have been reported previously in T2DM patients, first immunophenotyping was performed in healthy subjects (n=13) and T2DM (n=16) patients by using flow cytometry and C-reactive protein (CRP) measurement, a key marker for low-grade inflammatory state and cardiovascular risk (summarized in FIG. 7). Both leukocyte and neutrophil counts were higher in T2DM patients as compared to healthy subjects (P<0.001), indicating increased inflammatory responses in vivo (FIG. 4A, B). Average neutrophil ROS level (FIG. 4C) and CD11b expression (FIG. 4D) were also elevated in T2DM group (P<0.01), thus confirming more pronounced neutrophil activation in T2DM patients. Interestingly, there was a significant downregulation of neutrophil PGSL-1 expression in T2DM patients (P<0.05) (FIG. 4E). This was well correlated with neutrophil ROS level (FIG. 4F) and CD11b expression (FIG. 4G) in both healthy and T2DM patients as lower PSGL-1 expression was associated with increasing neutrophil activation. Negligible differences in PSGL-1 and CD11b expression were observed between DFF-sorted neutrophils and neutrophils washed with centrifugation in T2DM patients, further validating DFF as an efficient neutrophil purification technology for downstream assays or point of care testing. Besides neutrophils, downregulation of PSGL-1 expression was also observed in monocytes of T2DM patients (P<0.01) which warrants further studies to provide insights in monocyte-endothelial interactions and cardiovascular complications in T2DM patients. Taken together, these results clearly indicate proinflammatory situation in T2DM patients with the increased presence of activated neutrophils which can contribute to chronic inflammatory conditions.

Figure 5:
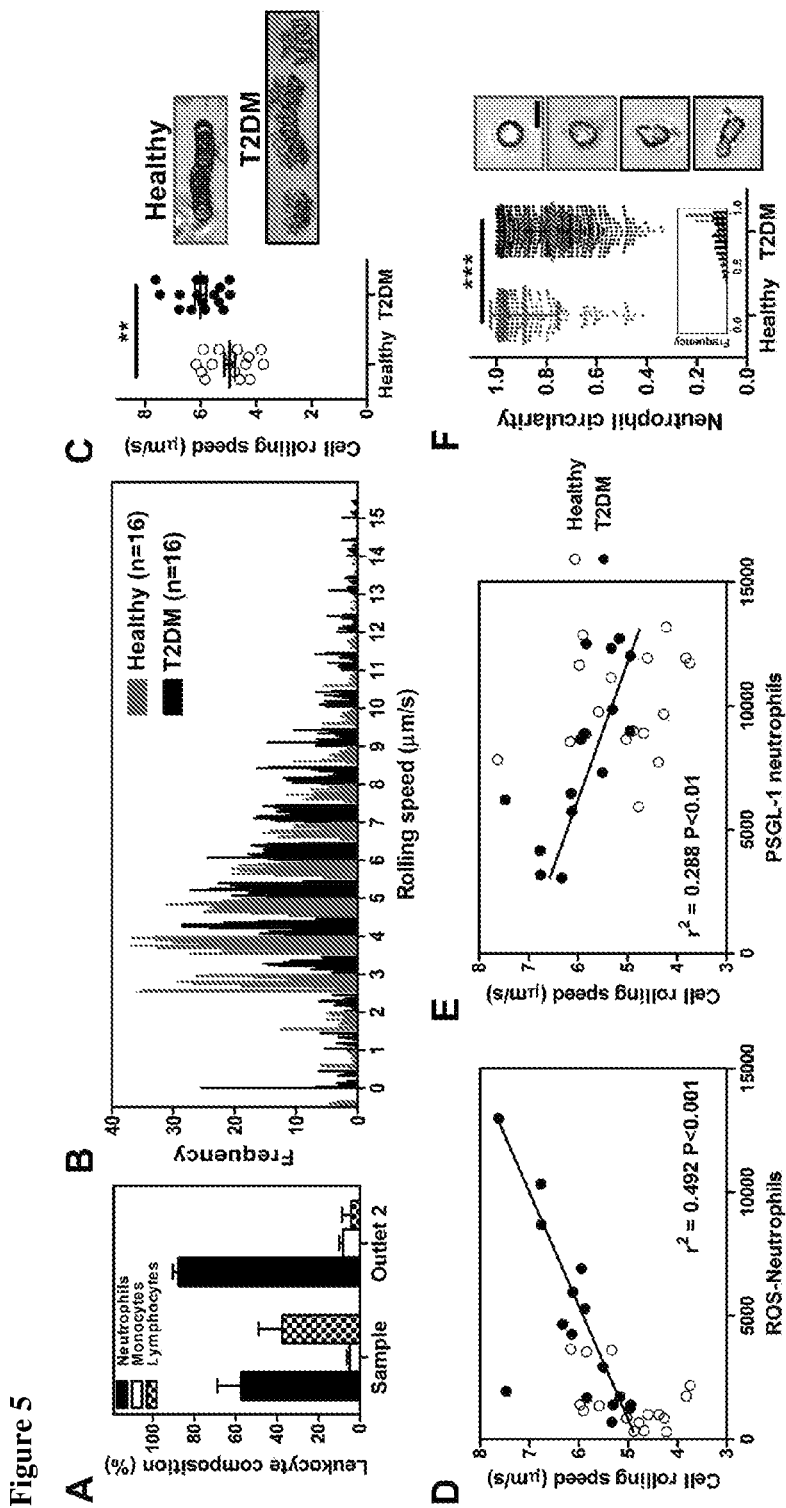
FIG. 5 shows neutrophil rolling in T2DM patients. (A) High purity of DFF-sorted neutrophils (~90%) from T2DM patients. Mean±s.d. from n=6. (B) Frequency distribution and (C) average rolling speed of neutrophils from healthy (n=16) and T2DM patients (n=16) in microchannel functionalized with E-selectin. Mean±s.e.m. *P<0.05. Representative images overlay of neutrophil rolling trajectories in healthy and T2DM patients. Correlation of average rolling speed with neutrophil (D) intracellular ROS level and (E) PSGL-1 expression. (F) Neutrophil circularity of healthy and T2DM patients. Mean±s.d. n=300 cells (from 5 healthy controls) and 500 cells (from 7 T2DM patients). ***P<0.001. Inset plot shows frequency distribution of neutrophil circularity. Representative brightfield images (60× magnification) illustrating neutrophil shape differences from healthy (grey box) and T2DM (black box) patients.

Current microfluidic rolling assays are limited by design complexity and conventional leukocyte isolation methods prior assay. To characterize neutrophil rolling phenotype in T2DM patients, neutrophils were isolated from healthy subjects (n=13) and T2DM (n=16) patients using the developed DFF microfluidic technology and measured their rolling speed on E-selectin in a microfluidic assay. As expected, high neutrophil purity (~90%) was achieved in outlet 2 of the spiral device when processing blood samples from T2DM patients (FIG. 5A). Neutrophil rolling speed varied between healthy and T2DM patients as evident by a shift towards higher rolling speed frequency distribution for T2DM patients (FIG. 5B). This gave rise to higher average rolling speed in T2DM patients (6.01±0.21 µm/sec (T2DM) vs. 5.04±0.23 µm/sec (healthy) $P<0.05$) and the rolling trajectories of T2DM neutrophils were more discontinuous and irregular as compared to healthy neutrophils (FIG. 5C). Average rolling speed was strongly correlated to neutrophil ROS level (FIG. 5D) and PSGL-1 expression ($P<0.001$) (FIG. 5E) but not CD11b in both healthy subjects and T2DM patients, suggesting a key role of PSGL-1 in mediating leukocyte rolling during inflammation. Neutrophil rolling pattern was compared in blood samples obtained using venipuncture or fingerprick from the same patient. Negligible differences in neutrophil rolling speed were observed between different blood sampling methods ($P\sim0.35$-$0.68$), indicating the robustness of the developed microfluidic strategies used for neutrophil sorting and functional phenotyping. Lastly, neutrophil morphology was characterized based on the neutrophil circularity (NC) index. As shown on FIG. 5F, DFF-sorted healthy neutrophils were mostly circular (~76% of cells with NC>0.85) while neutrophils from T2DM patients were more heterogeneous in shape, with a higher number of elongated cells (~55% of cells with NC 0.5~0.8) present. Such cytoplasmic prolongations may be caused by neutrophil activation which is known to affect cell morphology [Lavoie-Lamoureux, A. et al. *Am J Physiol Lung Cell Mol Physiol* 299, L472-L482 (2009)]. In summary, the DFF neutrophil purification technology was successfully validated in a cohort of healthy subjects and T2DM patients and clear evidence is provided that healthy and diabetic neutrophils possess distinct activation profiles and cell morphologies which affect their rolling phenotype on E-selectin.

Figure 6:
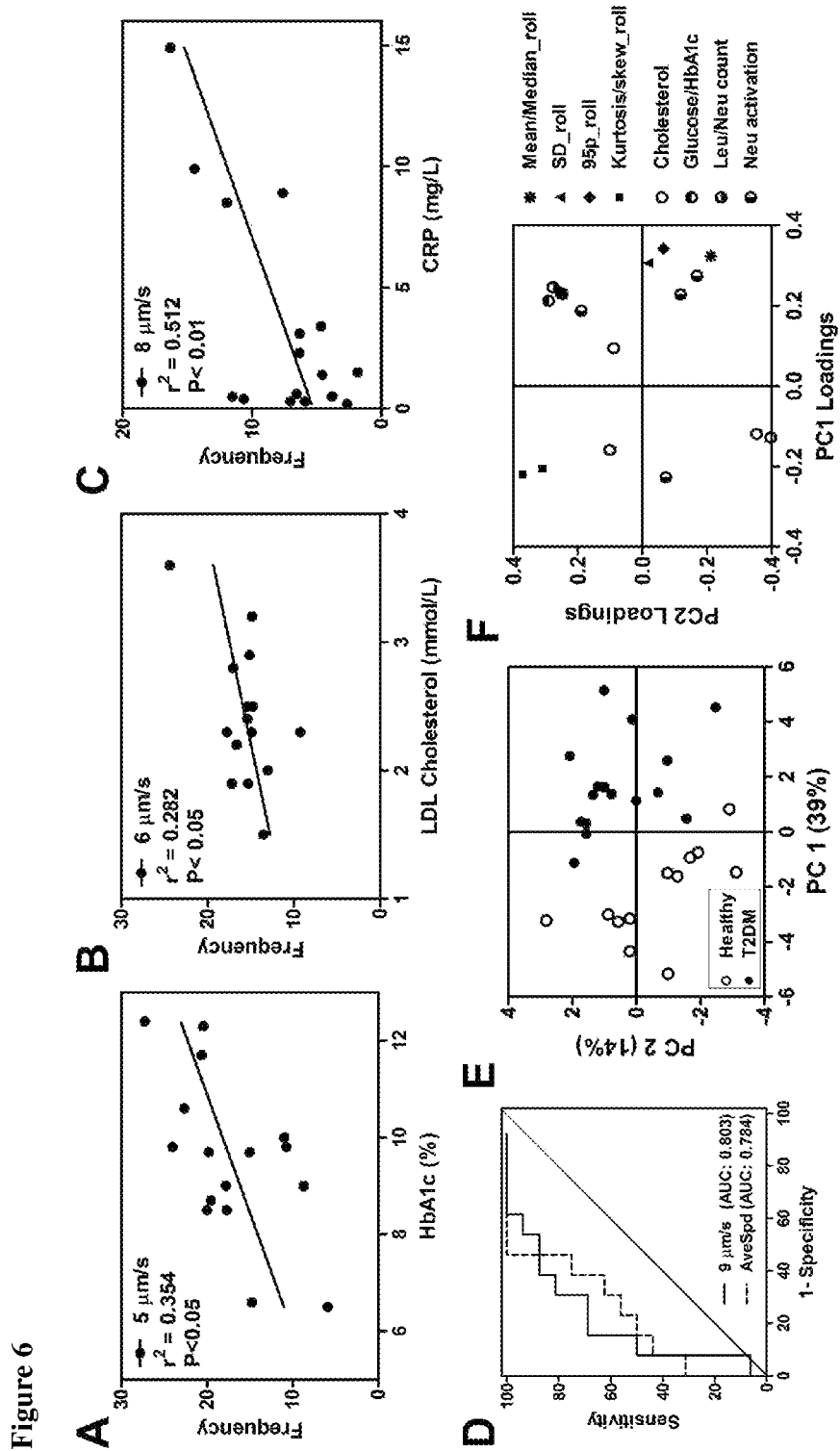
FIG. 6 shows neutrophil rolling phenotype as a functional biomarker for T2DM testing. Correlation of specific rolling speed frequency with (A) HbA1c (%), (B) LDL cholesterol and (C) C-reactive protein (CRP). (D) ROC analysis of patient data using average rolling speed and rolling speed frequency at 9 µm/sec. (E) PCA score plot shows well separation of healthy and T2DM patients on the $1^{st}$ principle component. (F) Loadings plot shows the contribution of each metric to the $1^{st}$ and $2^{nd}$ principle component score values.
Figure 9:
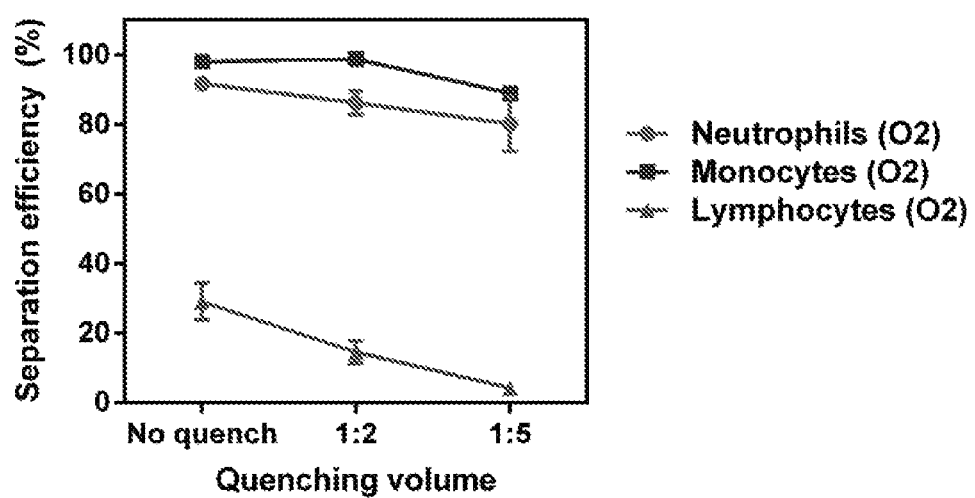
FIG. 9 shows the dependence of the ratio of purified cell types (cell size dependent) and volume of dilution buffer used for diluting the lysed whole blood sample.
Figure 10:
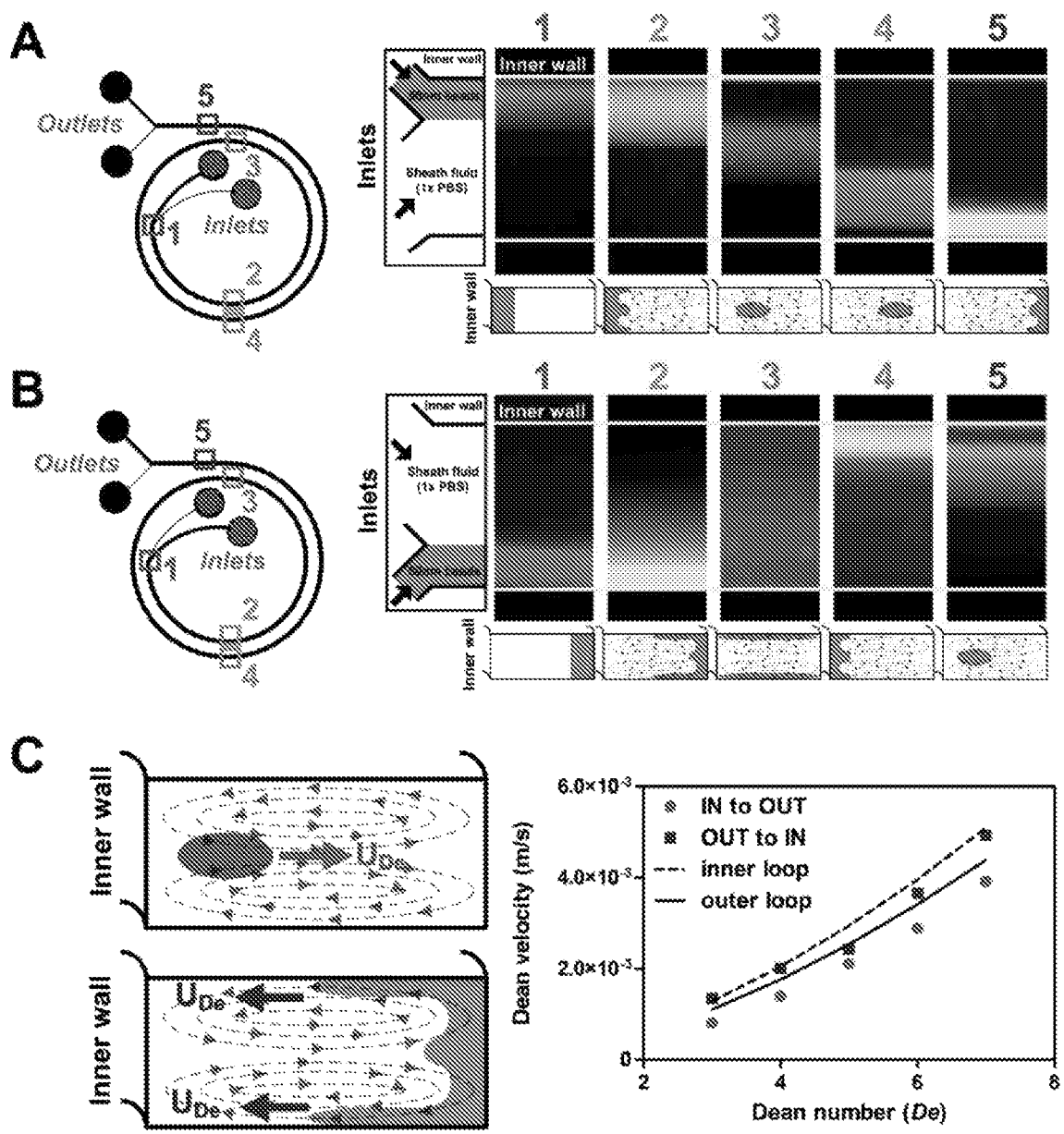
FIG. 10 shows the direct visualization and characterization of particle Dean migration in spiral microchannel. 50 nm fluorescent bead sample was introduced at the (A) inner wall or (B) outer wall at the inlet region. Average fluorescent stacked images indicate 50 nm bead positions along the channel. Yellow lines indicate positions of channel wall. Corresponding schematic images of channel cross section illustrate distinct differences in bead migration pattern depending on initial position of beads. (C) Higher Dean migration velocities were measured when particles recirculate from outer towards inner wall at the top and bottom of the channel (blue) as compared to particle migration along the channel midline from inner to outer wall (red). The experimentally measured Dean velocities were in good agreement with analytical values based on Ookawara et al. [Ookawara, S. et al. Chemical Engineering Science, 2006. 61(11): p. 3714-3724] Dean velocity equation.

After having established that neutrophils from T2DM patients rolled faster on E-selectin as compared to healthy subjects, it was determined if these functional differences can be associated to clinical conditions by analyzing rolling speed frequencies in T2DM patients that are higher than the average rolling speed of healthy subjects (≥5 µm/sec). It is likely that patients with higher cardiovascular risk factors have faster rolling neutrophils due to increased level of low-grade inflammation. Indeed, higher hemoglobin A1c (HbA1c) level corresponded to higher frequency for rolling speed 5 µm/sec in T2DM patients (FIG. 6A), and low-density lipoprotein (LDL) cholesterol and CRP levels were also associated with increasing frequency of faster rolling neutrophils at 6 and 8 µm/sec, respectively (FIG. 6B,C). These relationships clearly illustrate the importance of glucose and cholesterol metabolism in neutrophil activation which can affect neutrophil functionality (cell rolling) and thus attenuate leukocyte recruitment/response to inflamed endothelium. To further assess the clinical efficacy of neutrophil rolling speed as a functional biomarker in diabetes testing, it was shown that the rolling speed frequency (5 µm/sec) was a more sensitive indicator for HbA1c (%) than fasting glucose level in T2DM patients. Analysis of the receiver operating characteristics (ROC) of the patient data using a diagnostics cutoff of rolling speed frequency at 9 µm/sec yields a sensitivity and specificity of ~81% and ~70%, respectively (FIG. 6D). Principal component analysis (PCA) on clinical measurements (FIG. 7) and rolling speed distributions was next performed which indicated well separation of healthy and T2DM patients by the 1st principle component score (FIG. 6E). Multiple parameters including mean, median (Mean/Median_roll), standard deviation (SD_roll), skewness and kurtosis (Kurtosis/skew_roll) were used to describe the distribution characteristic of the neutrophils rolling speed. Rolling speeds greater than 95 percentile were averaged (95p_roll) and used to capture distribution on the right tail. In addition, PCA analysis also revealed that rolling speed and its distribution characteristic have strong contributions in discerning diabetes phenotype, as judged by the large magnitude in the 1st principle components loadings (FIG. 6F). Lastly, the effects of established vascular risk modifying drugs including metformin and pravastatin were studied on rolling phenotype of healthy neutrophils. These drugs are commonly used in diabetic patients as well as patients with a dysmetabolic state (i.e. pre-diabetes, CHD) and have additional anti-inflammatory effects that reduce the risk of developing diabetes [Deans, K. A. & Sattar, N. *Diabetes Technol Ther* 8, 18-27 (2006)]. They have been described to alter neutrophil chemotaxis and phagocytic activities [Park, D. W. et al. *Mol. Med.* 19, 387-398 (2013); Dunzendorfer, S. et al. *Circ Res* 81, 963-969 (1997)] and are thus likely to affect other migratory responses in neutrophil-endothelial interactions. To avoid prior exposure to these medications, the experiments were performed using healthy subjects and the DFF-purified neutrophils were incubated with metformin (1 mM) and pravastatin (20 µM) for 1 h before microfluidic rolling assay. Average rolling speed of both drug-treated neutrophils were higher than controls (untreated) in all paired observations ($P<0.05$), which suggests rapid and active alteration of neutrophil rolling phenotype and its potential as an inflammatory functional marker for drug monitoring.

Example 2: Separation of Small Micro/Nanoparticles Using Microfluidics Using a 2-Outlet Device The microfluidic devices are fabricated in polydimethylsiloxane (PDMS) using standard soft lithography techniques. The developed microdevice consists of a 2-inlet, 2-outlet spiral microchannel (300 µm (w)×60 µm (h)) with a radius of 0.5-0.6 cm and a total length of 6.5 cm. The sample (50 µm wide) and sheath (250 µm wide) inlets are fixed at the outer and inner wall of the channel, respectively. For outlet bifurcation, the smaller outlet channel at channel inner wall is designed to collect smaller particles (outlet 1) while larger particles are collected at the larger outlet (outlet 2).

During device operation, bead sample is pumped into the outer inlet while sheath fluid (1×PBS) is pumped through the inner inlet at a higher flow rate (1:5) to confine the sample stream near the outer wall. To ensure the absence of inertial focusing in our device, beads of smaller diameters (50 nm, 1 µm, 2 µm and 3 µm) were chosen such that they would not undergo inertial focusing in the device ($a_p/h \ll 0.07$). As the beads traverse through the channel, they experience lateral drag forces ($F_D$) and migrate towards the inner wall due to inherent Dean vortices. Near the inner wall region, the migrating beads are subjected to additional wall induced inertial lift forces ($F_{WL}$), resulting in a size-dependent transient position before recirculating back towards the outer wall. Interestingly, larger beads experience increasing wall induced inertial lift forces and the transient equilibrating positions are further away from the inner wall. By controlling the channel fluidic resistance off-chip, the subtle difference in Dean transient position of beads of different sizes can be exploited for separation of closely-sized small particles.

To understand the Dean migration profile of small particles along the channel, a microdevice was designed with the same geometry and channel dimensions except that the sample inlet is fixed at the inner wall instead of the outer wall. Fluorescent 50 nm bead solution was pumped into both devices at the same flow conditions and their Dean-induced lateral migration patterns were characterized by imaging at different positions along the channel (FIG. 10A,B). Experimental data clearly showed a difference in Dean migration profile of the 50 nm beads. When the beads were initially introduced at the inner wall, they would migrate along the channel midline tightly as a band towards the outer wall. On the contrary, beads initially at the outer wall would migrate along the top and bottom of the channel towards the inner wall. The difference in lateral positions were used to calculate the Dean migration velocities of particles which were in in good agreement with the analytical values based on Ookawara et al. Dean velocity equation (FIG. 10C).

Figure 11:
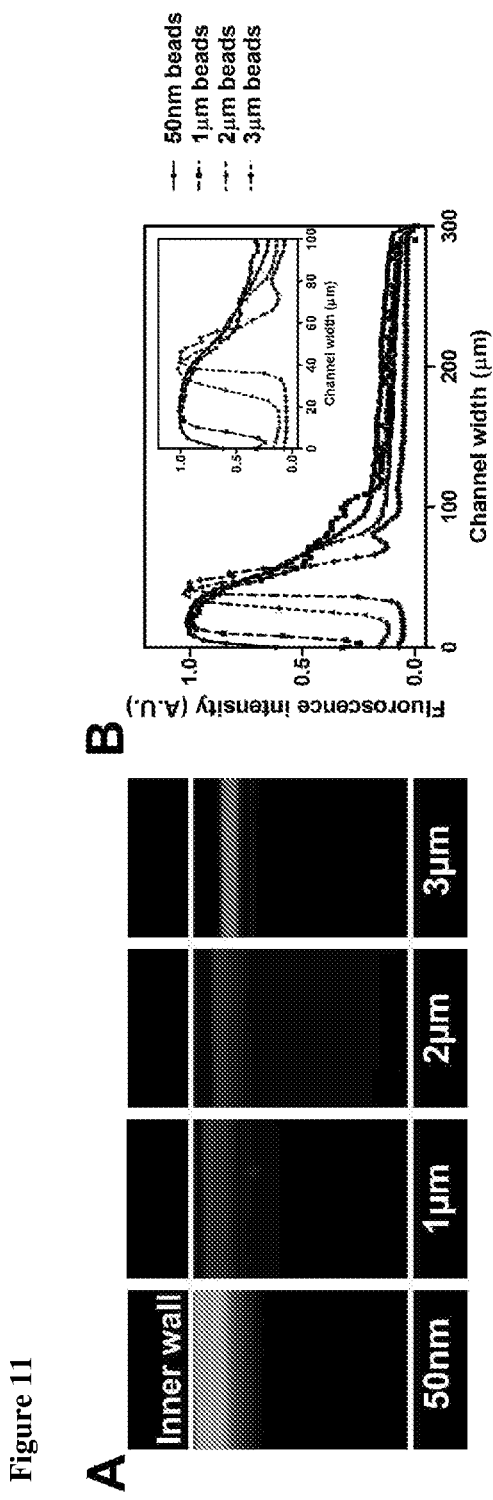
FIG. 11 shows the size-dependent transient position of beads during Dean migration at the inner wall region. Average fluorescent (A) stack images (pseudo coloured) and (B) intensity linescans indicating inner wall transient position for beads of different sizes (50 nm, 1 µm, 2 µm and 3 µm) during Dean migration from outer wall towards inner wall. Yellow lines indicate positions of channel wall. Larger beads experience increasing wall induced inertial lift forces, resulting in transient equilibrating positions further away from the inner wall. (Inset in B shows magnified view of the intensity linescans at the inner wall region 0-100 µm).

To characterize the difference in Dean transient position of beads at the inner wall, beads of various diameters (50 nm, 1 µm, 2 µm and 3 µm) were separately introduced into the device at different flow rates. As shown on FIG. 11, the smallest 50 nm beads migrated completely towards the inner wall due to negligible FWL. Larger beads experience increasing FWL, resulting in transient equilibrating positions further away from the inner wall.

Figure 12:
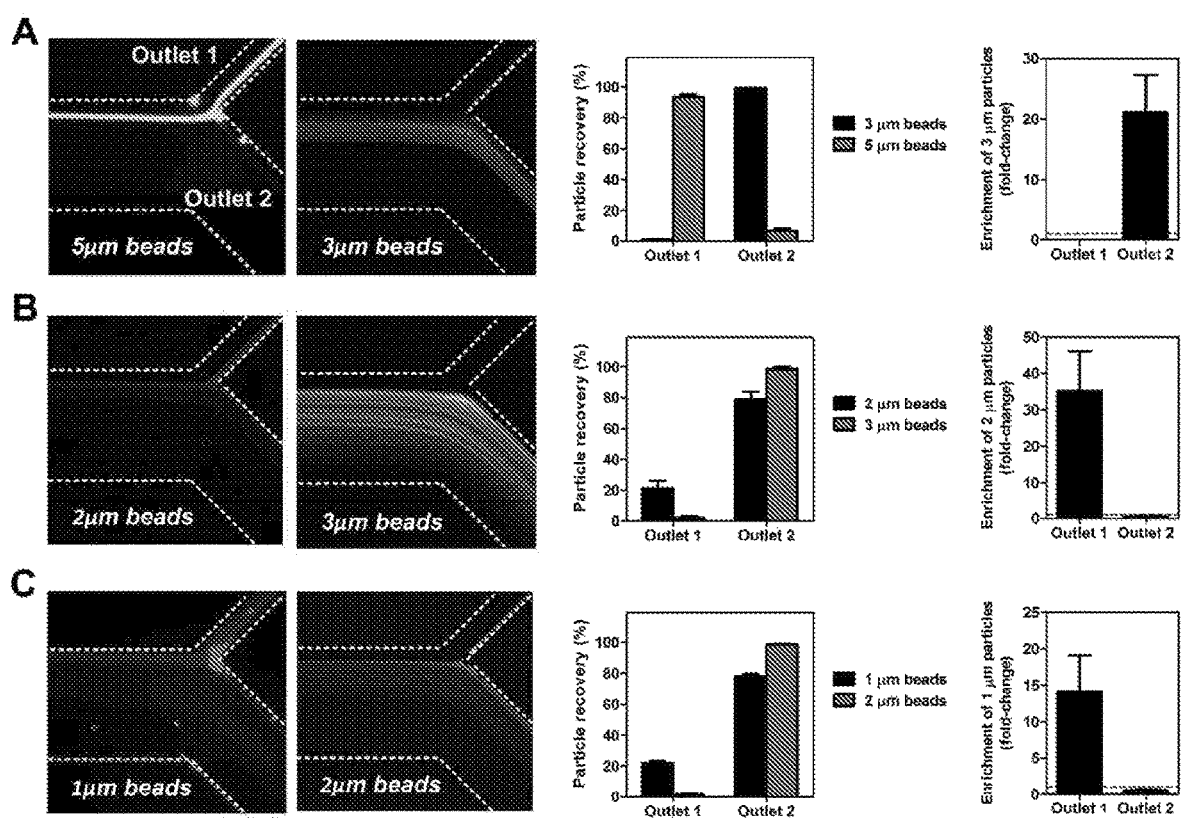
FIG. 12 shows high throughput separation of small microparticles with closely-spaced sizes. (A) Average fluorescent stack images showing equilibrating inner wall transient positions of (A) 5 µm (green) and 3 µm beads (red), (B) 3 µm (green) and 2 µm beads (red) and (C) 2 µm (green) and 1 µm beads (red) at optimized flow conditions. Yellow dotted lines indicate positions of channel outlet furcation. Separation efficiency and enrichment ratio of small particles are shown on right (Mean±sem, n=3).
Figure 13:
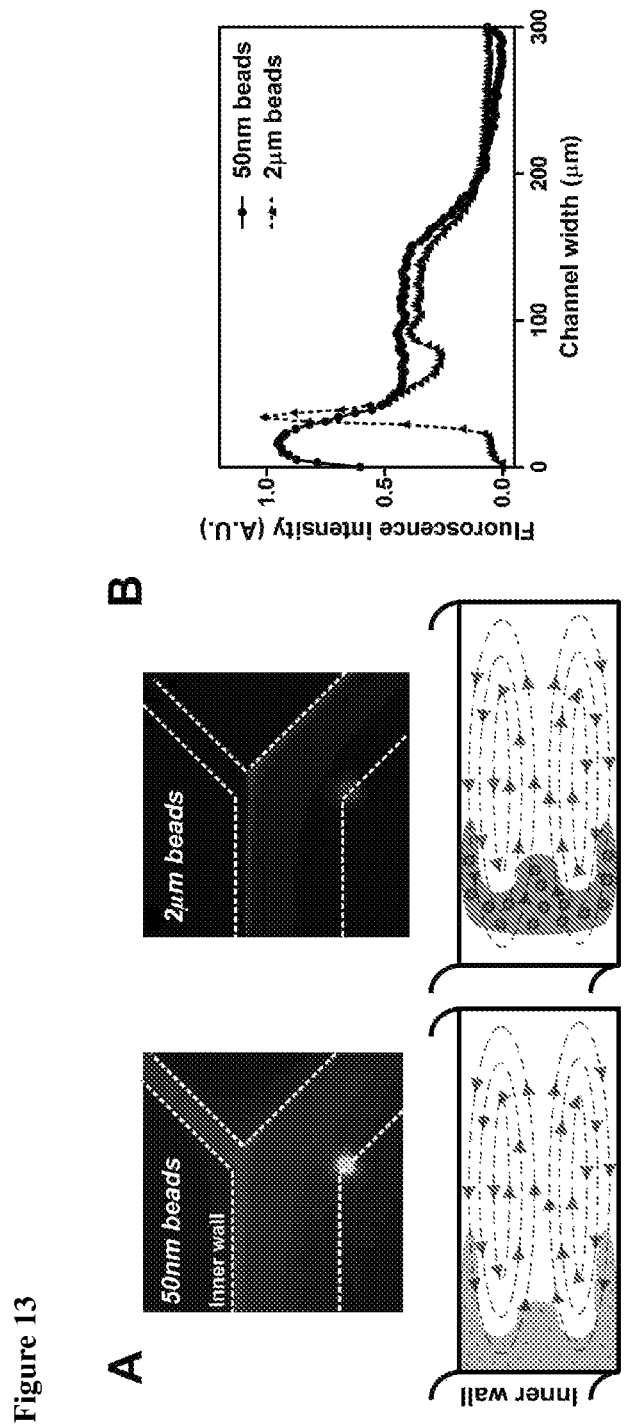
FIG. 13 shows the separation of nanoparticles and small microparticles. Average fluorescent (A) stack images and (B) intensity linescans indicate distinct differences in inner wall transient position for 50 nm and 2 µm beads during Dean migration from outer wall towards inner wall. Yellow dotted lines indicate positions of channel outlet furcation.

To demonstrate that this subtle difference in bead inner wall transient position can be used for separation of small particles with closely spaced sizes, bead mixtures of various combinations (5 µm and 3 µm beads; 3 µm and 2 µm beads; 2 µm and 1 µm beads) were processed by the spiral device at empirically determined optimized flow conditions. As shown on FIG. 12, the device was able to achieve binary sorting for all bead combinations by varying flow conditions and adjusting the outlet channel resistance. Small particles were significantly enriched (~10-30 fold) and continuously collected in outlet 1. The only exception is the sorting of 5 µm and 3 µm beads as 5 µm beads became inertially focused at inner wall (ap/h~0.08) while smaller 3 µm beads recirculated towards outer wall and were collected at outlet 2 instead). Similarly, sorting of 50 nm and 2 µm beads was successfully achieved which is important in nanoparticle synthesis or exosome-related studies (exosomes ~50 nm in size)(FIG. 13).

Example 3: Bacterial Sorting

Figure 14:
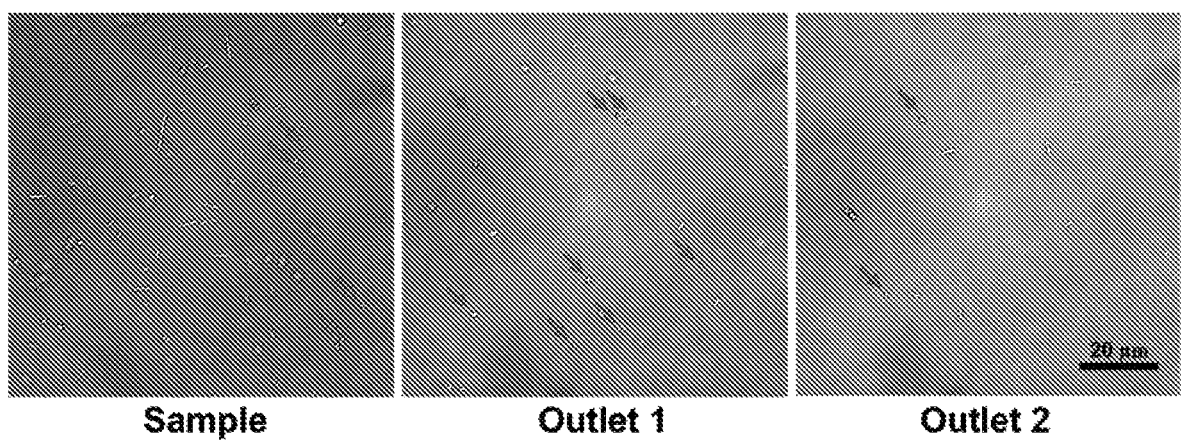
FIG. 14 shows optical images (100× magnification) illustrating separation and enrichment of S. aureus (red arrows) into outlet 1, while E. coli is sorted into outlet 2.
Figure 15:
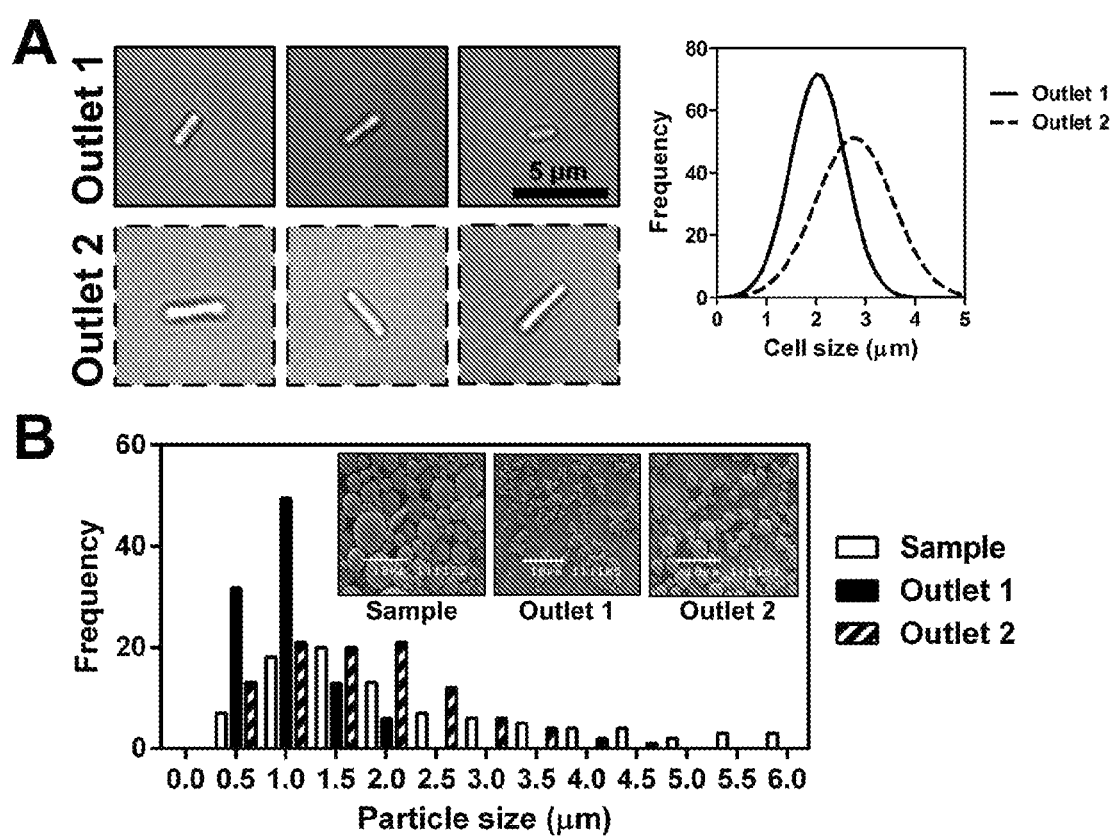
FIG. 15 shows size fractionation of E. coli using the developed spiral technology. Representative images (100× magnification) and frequency distribution (fitted Gaussian) illustrating distinct differences in sorted E. coli cell size in different outlets. ~50-80 bacteria were measured at each outlet. (B) Size fractionation of PLGA nanoparticles. Inset SEM images highlight distinct size differences between sample (inlet) and different outlets.

Based on the focusing mechanism in a 2-outlet spiral device, separation and enrichment of bacteria species was performed based on their cell size. As proof of concept, sample solution containing mixture of *E. coli* (rod shaped, ~2-4 µm long, 1 µm wide) and *S. aureus* (circular, ~1 µm diameter) was pumped into the device. The smaller *S. aureus* were sorted into outlet 1 while *E. coli* were recovered mostly in outlet 2 (FIG. 14). Interestingly, size fractionation of *E. coli* was observed as smaller *E. coli* (mean±SD; 2.03±0.46 µm) and larger *E. coli* (2.85±0.75 µm) were sorted into outlet 1 and 2, respectively (FIG. 15). This further illustrates the superior separation resolution of the present technology for bacterial sorting or diagnostics.

Example 4: Monocyte Sorting

Figure 16:
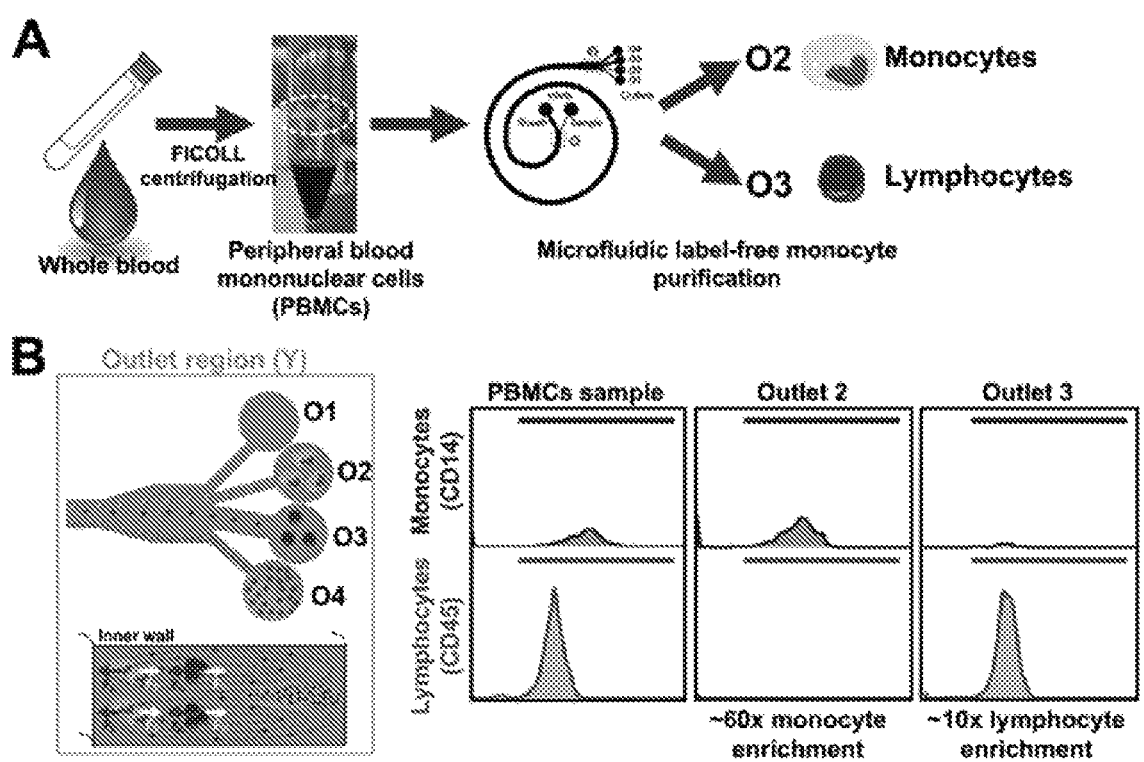
FIG. 16 shows a workflow for label-free fractionation of peripheral blood mononuclear cells (PBMCs) obtained from density centrifugation using Ficoll® Paque Plus. (B) Schematic illustration and flow cytometry analysis indicating efficient separation of monocytes and lymphocytes into outlet 2 and outlet 3, respectively, using DFF.
Figure 17:
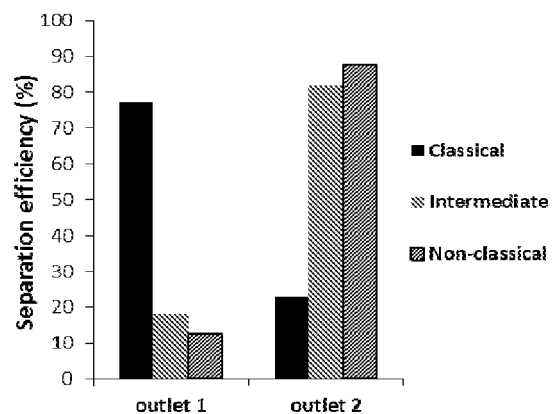
FIG. 17 shows a flow cytometry analysis of monocyte fractionation using a 2-outlet DFF spiral device. Classical monocytes are defined as CD14+(DAPI) and CD16-(FITC). Intermediate monocytes are defined as CD14+/CD16+. Non-classical monocytes are defined as CD14-/CD16+. Non-classical monocytes are enriched 2-3 fold in outlet 2.
Figure 17:
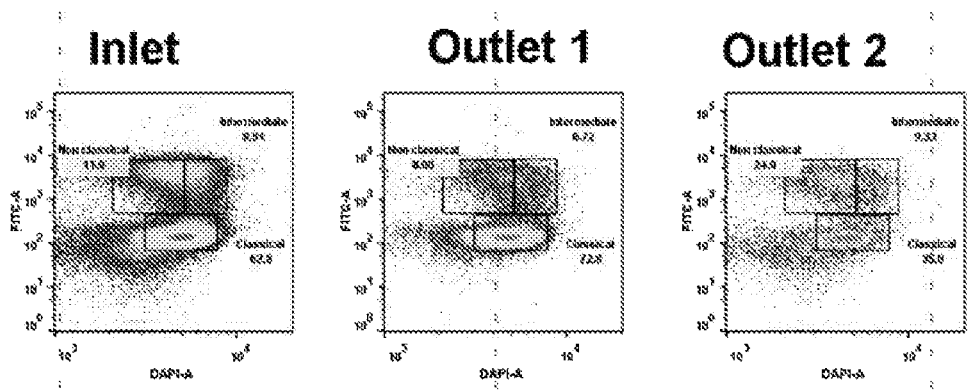
Figure 18:
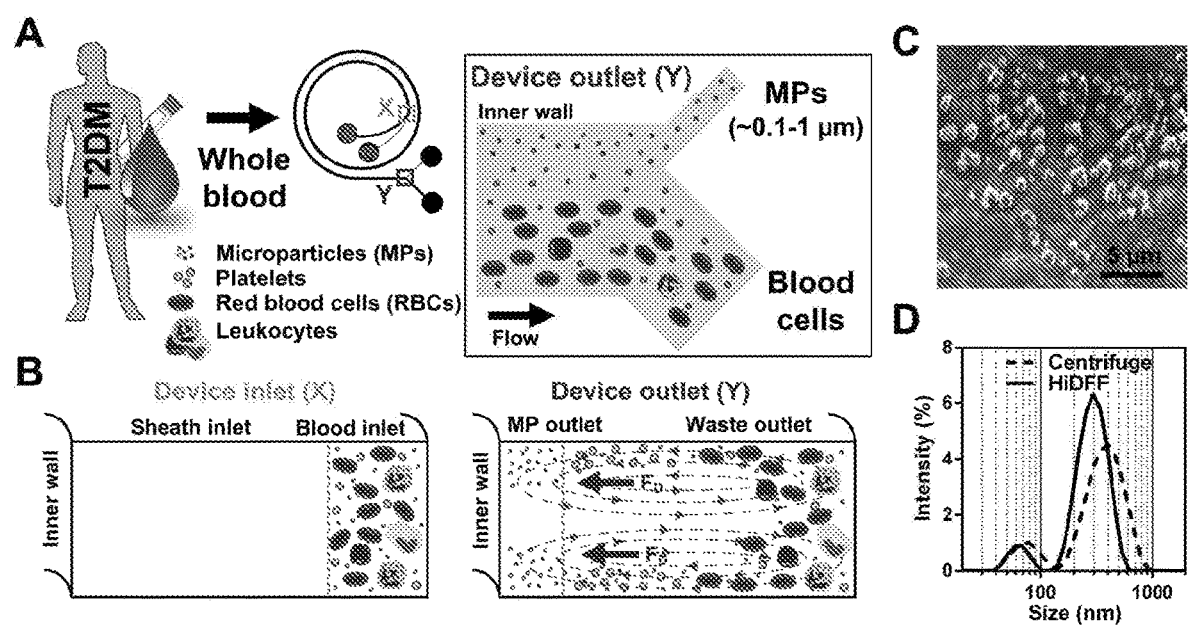
FIG. 18 shows a workflow to recover microparticles (MP) from blood. (A) Single step microparticles isolation from whole blood directly using Dean Flow Fractionation (DFF). Under the influence of Dean vortices in spiral microchannel, microparticles (MPs, ~0.1-1 µm) and platelets (~2-3 µm) migrate laterally towards inner wall. The innermost transient position of the smaller MPs is closer than platelets at the inner wall, thus resulting in efficient MPs purification with superior resolution. (B) Schematic illustration of the channel cross section at device inlet (X) and outlet (Y). MPs are continuously sorted into the inner outlet (MP outlet), while platelets and blood cells are collected as waste. (C) SEM images of the sorted MPs from blood. (D) DLS measurement of MPs size isolated from blood using DFF and conventional centrifugation.
Figure 19:
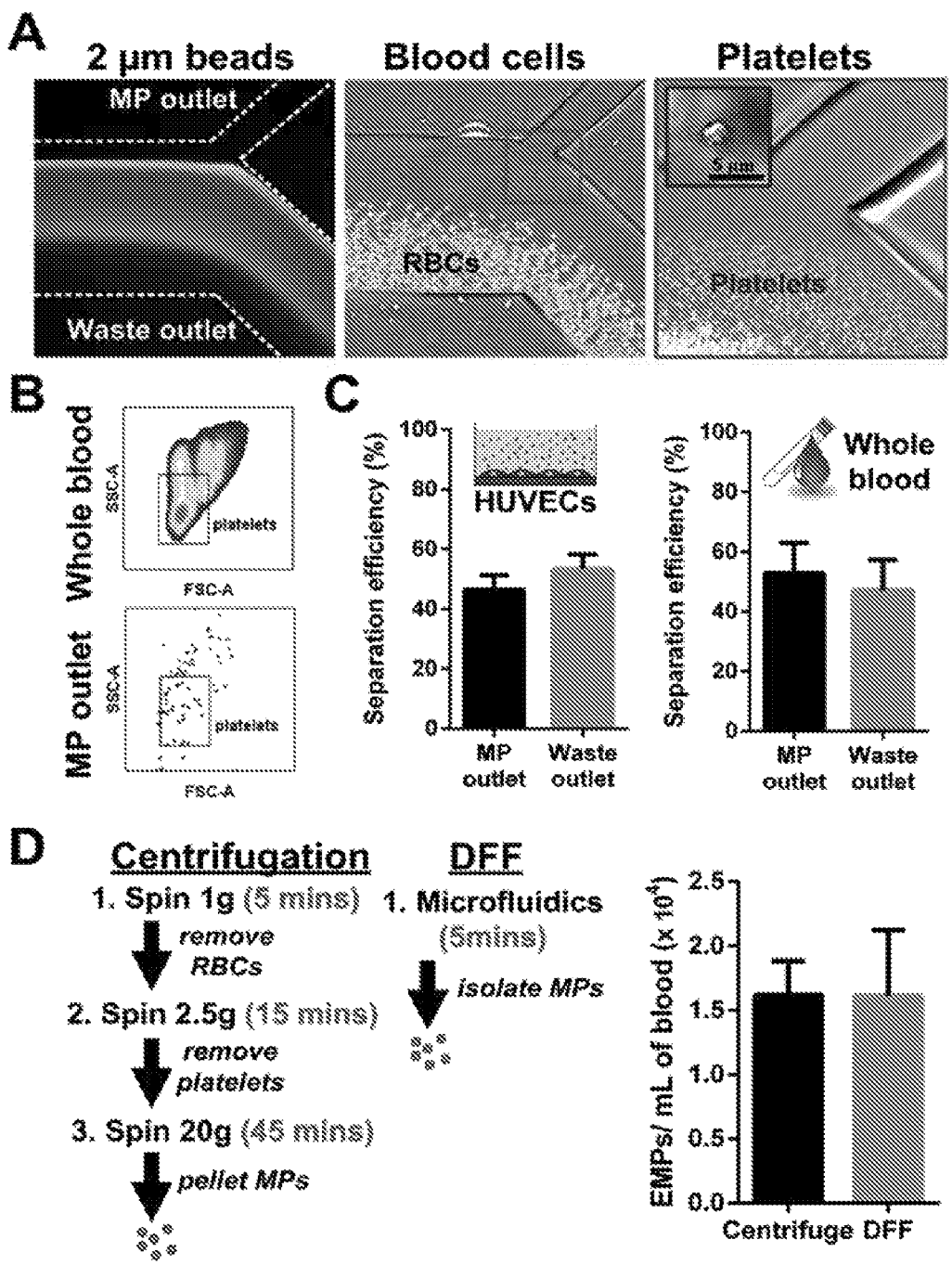
FIG. 19 shows (A) fluorescent and high speed images illustrating equilibrium position of 2 µm beads, blood cells and platelets. Flow rate is optimized based on 2 µm beads focusing into the waste outlet. Larger RBCs experience significant drag forces and remain close to outer wall. Platelets equilibrate similar to 2 µm beads and are sorted into the waste outlet. Inset (blue box) is a representative image of a platelet at 60× magnification. (B) Flow cytometry analysis (forward and side scatters) indicate negligible platelet contamination in MP outlet. (C) Characterization of MPs separation efficiency using endothelial cell culture (HU-VECs) and whole blood. (D) Comparison of MPs isolation efficiency from whole blood using conventional multi-step centrifugation and DFF.
Figure 20:
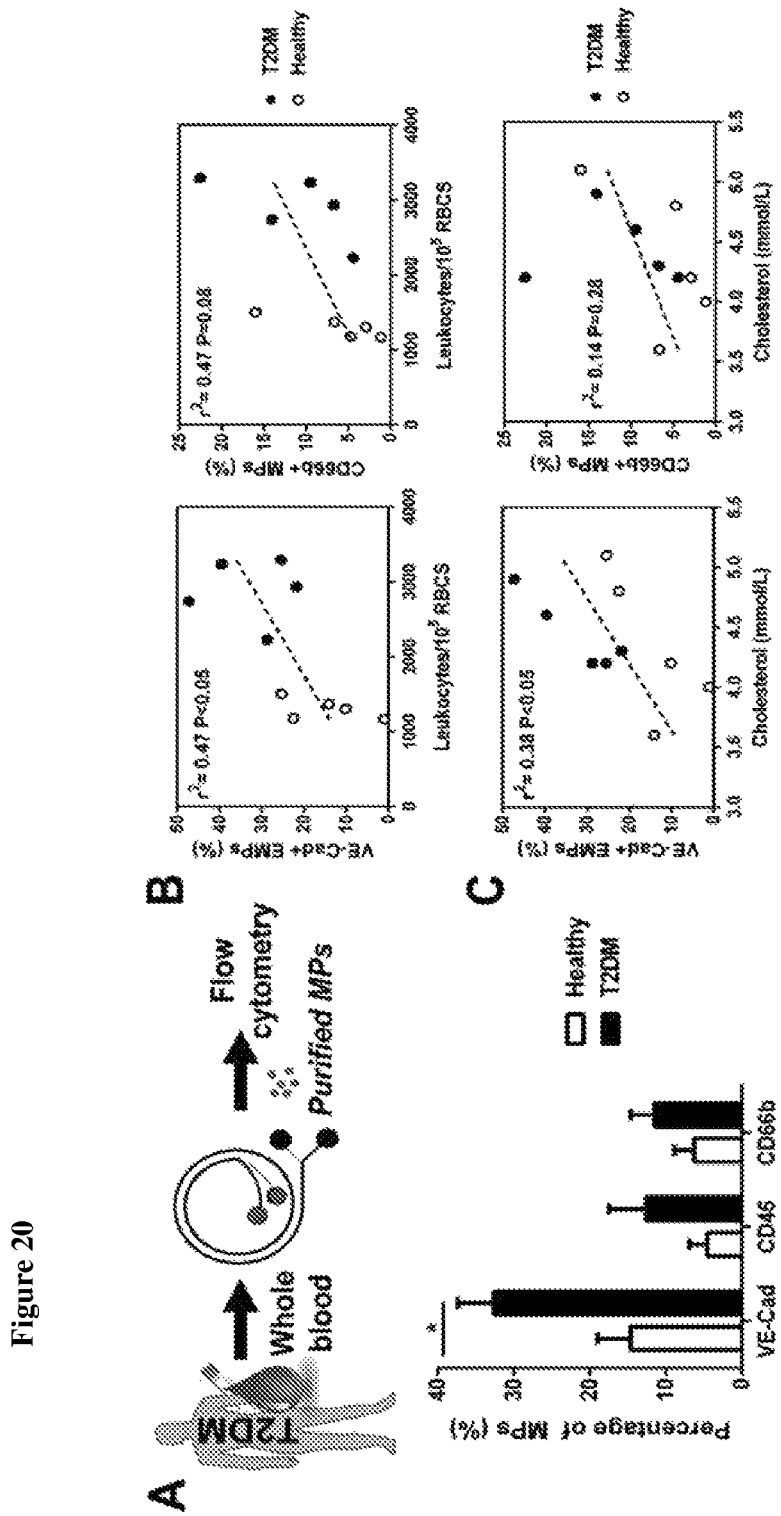
FIG. 20 shows (A) clinical validation of the developed DFF technology to isolate blood-borne MPs from patients with type 2 diabetes mellitus (T2DM) for flow cytometry analysis. Higher percentage of endothelial MPs (VE-Cad+), leukocyte-derived MPs (CD45+) and neutrophil-derived MPs (CD66b+) are detected in T2DM patients as compared to healthy subjects (n=5 in each group), indicating elevated vascular and systemic inflammation. Association of endothelial MPs and neutrophil-derived MPs with (B) leukocyte count and (C) cholesterol level in healthy and T2DM patients.

Monocytes have been fractionated from a blood sample according to the workflow of FIG. 16. The enriched fraction of monocytes has been sorted in a 4-outlet microfluidic device and sorting has been investigated by flow cytometry (FACs) analysis (FIG. 17).

Figure 2:
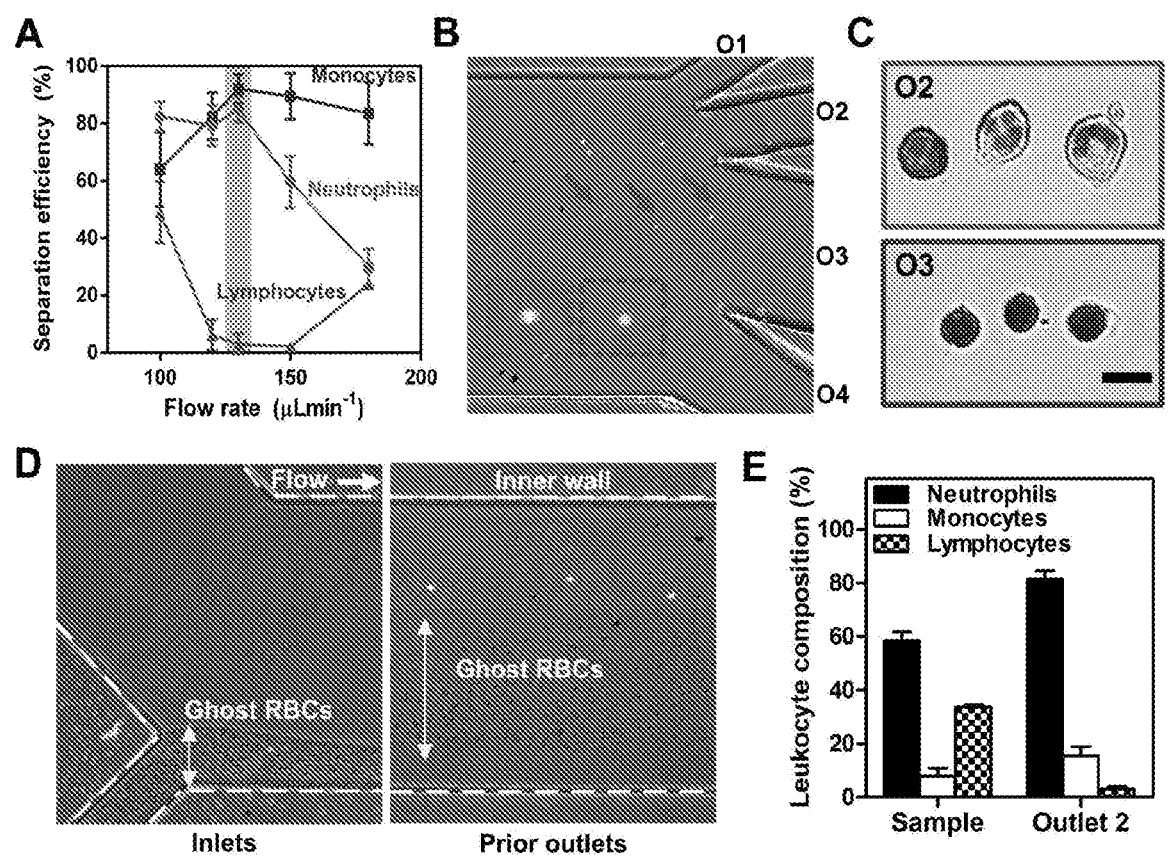
FIG. 2 shows a neutrophil purification using DFF microdevice. (A) Flow rate characterization on neutrophil sorting in outlet 2 of spiral device. Optimal separation was achieved at 130 µLmin$^{-1}$ (highlighted). Mean±s.d. from n=2-4. (B) Representative high speed images showing separation of larger neutrophils (red arrows) and smaller lymphocytes (green arrows) into different outlets. Enlarged inset images (dotted boxes) illustrate the cell size difference. (C) Wright-Giemsa staining of sorted neutrophils from outlet 2 (red box) and lymphocytes from outlet 3 (green box). (D) Representative high speed images of lysed blood processing and separation of ghost RBCs (yellow arrows) and leukocytes (red arrows). (E) Leukocyte composition of inlet sample and outlet 2 post DFF sorting. Mean±s.d. from n=3.
Figure 3:
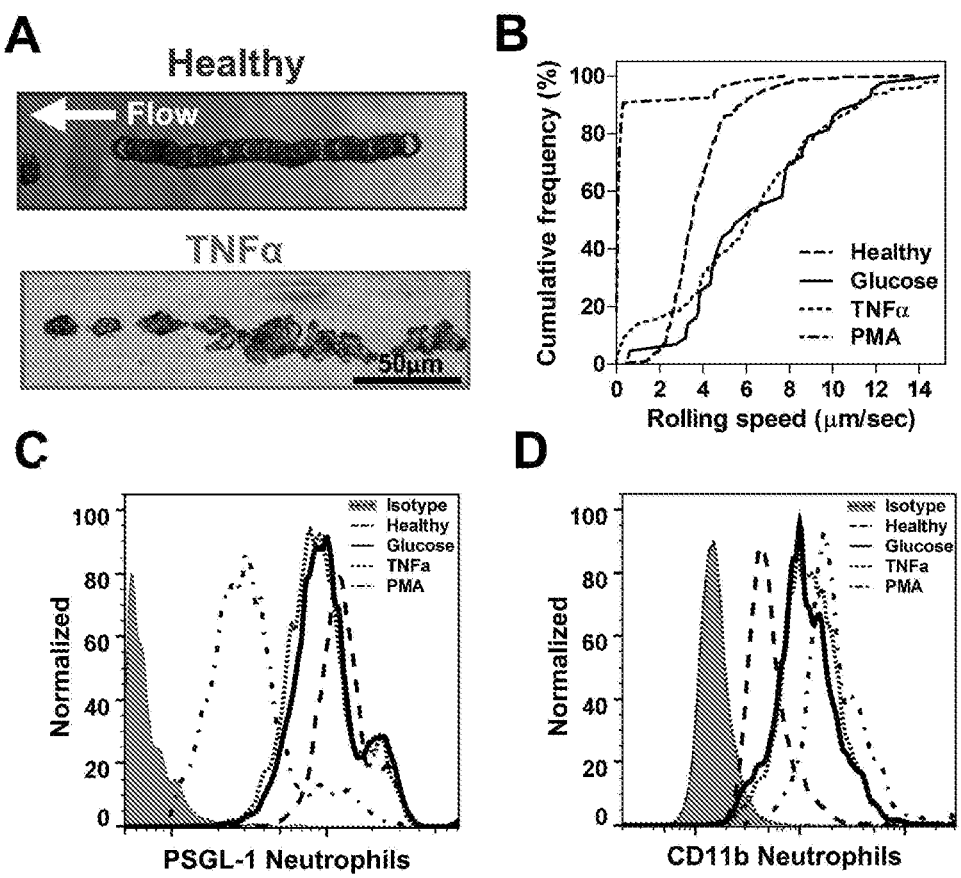
FIG. 3 shows neutrophil rolling on E-selectin. (A) Image overlay (60× magnification) from captured cell rolling videos highlight distinct differences in rolling trajectories between healthy and TNF-α-treated neutrophils. (B) Cumulative frequency curves of neutrophil rolling speed for healthy, glucose-treated (30 mM), TNF-α-treated (10 ng/mL) and PMA-treated (1 µM) neutrophils. The rolling speeds for all treated groups (~50-200 cells in each group) were significantly different as compared to healthy neutrophils (P<0.005). Flow cytometric analysis of (C) PSGL-1 and (D) CD11b expression on healthy and treated neutrophils. Cells were incubated with mouse APC anti-human PSGL-1 IgG2a/mouse APC IgG2a isotype and FITC mouse anti-human CD11b (activated) IgG1/FITC mouse IgG1 isotype.

Example 5: Single Step Isolation of Endothelial Microparticles from Whole Blood for Rapid Vascular Health Profiling in Diabetes Patient Using the technology of the present invention, a rapid (5 min), single-step microfluidic platform is described to isolate microparticles (MPs) directly from whole blood efficiently for downstream processing and analysis. The clinical utility of this technology was further demonstrated by enumerating and examining MPs levels in type 2 diabetes mellitus (T2DM) patients and healthy subjects (FIG. 1-3).

The invention has been described broadly and generically herein. Each of the narrower species and subgeneric groupings falling within the generic disclosure also form part of the invention. This includes the generic description of the invention with a proviso or negative limitation removing any subject-matter from the genus, regardless of whether or not the excised material is specifically recited herein. Other embodiments are within the following claims. In addition, where features or aspects of the invention are described in terms of Markush groups, those skilled in the art will recognize that the invention is also thereby described in terms of any individual member or subgroup of members of the Markush group.

One skilled in the art would readily appreciate that the present invention is well adapted to carry out the objects and obtain the ends and advantages mentioned, as well as those inherent therein. Further, it will be readily apparent to one skilled in the art that varying substitutions and modifications may be made to the invention disclosed herein without departing from the scope and spirit of the invention. The compositions, methods, procedures, treatments, molecules and specific compounds described herein are presently representative of preferred embodiments are exemplary and are not intended as limitations on the scope of the invention. Changes therein and other uses will occur to those skilled in the art which are encompassed within the spirit of the invention are defined by the scope of the claims. The listing or discussion of a previously published document in this specification should not necessarily be taken as an acknowledgement that the document is part of the state of the art or is common general knowledge.

The invention illustratively described herein may suitably be practiced in the absence of any element or elements, limitation or limitations, not specifically disclosed herein. Thus, for example, the terms "comprising", "including", "containing", etc. shall be read expansively and without limitation. The word "comprise" or variations such as "comprises" or "comprising" will accordingly be understood to imply the inclusion of a stated integer or groups of integers but not the exclusion of any other integer or group of integers. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by exemplary embodiments and optional features, modification and variation of the inventions embodied therein herein disclosed may be resorted to by those skilled in the art, and that such modifications and variations are considered to be within the scope of this invention.

The content of all documents and patent documents cited herein is incorporated by reference in their entirety.

The invention claimed is:

1. A method for separating blood cells, wherein the method comprises:
   lysing red blood cells of a blood sample;
   diluting said blood sample to provide a diluted sample;
   providing a microfluidic device comprising a spiral-shaped flow channel having at least a first end and a second end,
      wherein said spiral-shaped flow channel has two inlet ports at or near said first end and at least two outlet ports at or near said second end,
      wherein one of the two inlet ports is located at the inner wall of the spiral-shaped flow channel and the other inlet port is located at the outer wall of the spiral-shaped flow channel and at least one of the outlet ports is connected to a container allowing the storage of blood cells, and
      wherein the spiral-shaped flow channel has a height of 110-130 μm;
   introducing the diluted sample comprising lysed red blood cells into the inlet port located at the outer wall of the spiral-shaped flow channel and introducing a sheath fluid into the inlet port located at the inner wall of the spiral-shaped flow channel;
   driving said sample and the sheath fluid through the spiral-shaped flow channel; and
   recovering the blood cells in the at least one container connected to the at least one outlet port,
   wherein the at least two outlet ports comprise at least four outlet ports,
   wherein the spiral-shaped flow channel gradually expands to a width of about 1000 μm at the furcation of the outlet ports, and
   wherein a first outlet port covers the width 0-100 μm, a second outlet port covers the width 101-250 μm, a third outlet port covers the width 251-650 μm, and a fourth outlet port covers the width 651-1000 μm of the spiral-shaped flow channel defined from the inner wall towards the outer wall.

2. The method according to claim 1, wherein said method does not comprise a centrifugation step.

3. The method according to claim 1, wherein the sample is provided from a finger prick or generated from venipuncture.

4. The method according to claim 1, wherein a Reynolds number (Re) of the sample flowing through the spiral-shaped flow channel is 50-100.

5. The method according to claim 1, wherein the spiral-shaped flow channel comprises one or more of the following:
   polydimethylsiloxane (PDMS);
   a width of 300-600 μm;
   a height of 110-130 μm;
   a total length of 7-13 cm; and
   combinations thereof.

6. The method according to claim 1, wherein the blood cells comprise one or more of the following selected from the group consisting of neutrophils, monocytes, lymphocytes, platelets, red blood cells, and combinations thereof.

7. The method according to claim 6, wherein the method further comprises
   recovering the neutrophils and the monocytes from the second outlet port, and/or
   recovering the lymphocytes from the third outlet port.

8. The method according to claim 1, wherein
   the flow rate of the sheath fluid is at least 5-fold higher than the flow rate of the diluted sample; and/or
   the flow rate of the diluted sample is 120-130 μL/min.

9. The method according to claim 1, wherein
   the blood cells are recovered in a buffer; and/or
   the blood sample is diluted at least 1:5 with a buffer.

10. A microfluidic device comprising:
    a spiral-shaped flow channel having at least a first end and a second end,
    wherein said spiral-shaped flow channel has two inlet ports at or near said first end and at least two outlet ports at or near said second end,
    wherein one of the two inlet ports is located at the inner wall of the spiral-shaped flow channel and the other inlet port is located at the outer wall of the spiral-shaped flow channel and at least one of the outlet ports is connected to a container allowing the storage of blood cells;
    wherein the spiral-shaped flow channel has a height of 110-130 μm,
    wherein the at least two outlet ports comprise at least four outlet ports,
    wherein the spiral-shaped flow channel gradually expands to a width of about 1000 μm at the furcation of the outlet ports, and
    wherein a first outlet port covers the width 0-100 μm, a second outlet port covers the width 101-250 μm, a third outlet port covers the width 251-650 μm, and a fourth outlet port covers the width 651-1000 μm of the spiral-shaped flow channel defined from the inner wall towards the outer wall.

11. A method for separating microparticles from blood cells, wherein the method comprises:
    lysing red blood cells of a blood sample;
    diluting said blood sample;
    providing a microfluidic device comprising a spiral-shaped flow channel having at least a first end and a second end,
       wherein said spiral-shaped flow channel has two inlet ports at or near said first end and at least four outlet ports at or near said second end,
       wherein the spiral-shaped flow channel gradually expands to a width of about 1000 μm at the furcation of the outlet ports,
       wherein a first outlet port covers the width 0-100 μm, a second outlet port covers the width 101-250 μm, a third outlet port covers the width 251-650 μm, and a fourth outlet port covers the width 651-1000 μm of the spiral-shaped flow channel defined from the inner wall towards the outer wall,
       wherein one of the two inlet ports is located at the inner wall of the spiral-shaped flow channel and the other inlet port is located at the outer wall of the spiral-shaped flow channel, wherein the first outlet port is connected to a first container allowing the storage of microparticles and at least one of the second, third, or fourth outlet port is connected to a second container allowing the storage of blood cells, and wherein the spiral-shaped flow channel has a height of 110-130 μm;

introducing the diluted sample comprising lysed red blood cells into the inlet port located at the outer wall of the spiral-shaped flow channel and introducing a sheath fluid into the inlet port located at the inner wall of the spiral-shaped flow channel;

driving said sample and the sheath fluid through the spiral-shaped flow channel; and recovering the microparticles from the first container connected to the first outlet port, wherein the microparticles have an average particle size ranging from about 0.1 μm to about 1 μm.

12. The method according to claim 1, wherein said method does not comprise a labeling step by which at least one type of blood cells is labeled with a marker molecule.

* * * * *